(12) United States Patent
Holzner et al.

(10) Patent No.: US 10,808,046 B2
(45) Date of Patent: Oct. 20, 2020

(54) METHOD FOR PRODUCING A PROPHYLACTIC ARTICLE

(71) Applicant: Semperit Aktiengesellschaft Holding, Vienna (AT)

(72) Inventors: Armin Holzner, Ternitz (AT); Wolfgang Kern, Seiersberg (AT); Jakob Cornelius Manhart, Giesshuebl (AT); Melahat Sahin, Leoben (AT); Raimund Schaller, Neunkirchen (AT); Sandra Schloegl, Stallhofen (AT)

(73) Assignee: Semperit Aktiengesellschaft Holding, Vienna (AT)

( * ) Notice: Subject to any disclaimer, the term of this patent is extended or adjusted under 35 U.S.C. 154(b) by 95 days.

(21) Appl. No.: 16/081,486

(22) PCT Filed: Mar. 2, 2017

(86) PCT No.: PCT/AT2017/060053
§ 371 (c)(1),
(2) Date: Aug. 31, 2018

(87) PCT Pub. No.: WO2017/147639
PCT Pub. Date: Sep. 8, 2017

(65) Prior Publication Data
US 2019/0092879 A1 Mar. 28, 2019

Related U.S. Application Data

(63) Continuation of application No. PCT/AT2017/060053, filed on Mar. 2, 2017.

(30) Foreign Application Priority Data

Mar. 4, 2016 (AT) .............................. A 50176/2016

(51) Int. Cl.
B29C 41/14 (2006.01)
C08C 19/25 (2006.01)
(Continued)

(52) U.S. Cl.
CPC .......... *C08C 19/25* (2013.01); *B29C 35/0805* (2013.01); *B29C 41/003* (2013.01);
(Continued)

(58) Field of Classification Search
None
See application file for complete search history.

(56) References Cited

U.S. PATENT DOCUMENTS 5,997,969 A * 12/1999 Gardon .............. A41D 19/0055
2/167
6,627,325 B1 * 9/2003 Ghosal ........................ C08J 5/02
428/500
(Continued)

FOREIGN PATENT DOCUMENTS

EP 1 209 186 A1 5/2002
EP 1 762 586 A2 3/2007
(Continued)

OTHER PUBLICATIONS

Chakraborty et al. "Epoxy-Resin-Cured Carboxylated Nitrile Rubber", J. Applied Polym. Sci. 1982, 27, 4561-4576. (Year: 1982).*
(Continued)

Primary Examiner — Robert S Loewe
(74) Attorney, Agent, or Firm — Collard & Roe, P.C.

(57) ABSTRACT

According to a method for the manufacture of a prophylactic article, especially of a glove, from a (carboxylated) diene rubber, at least one layer of a (carboxylated) diene latex is applied on a former and the (carboxylated) diene latex is cross-linked with a cross-linking agent, wherein a mercapto-functional siloxane polymer is used as cross-linking agent.

14 Claims, 6 Drawing Sheets

(51) Int. Cl.
*C08J 5/02* (2006.01)
*C08J 3/26* (2006.01)
*B29C 35/08* (2006.01)
*B29C 41/00* (2006.01)
*B29C 41/46* (2006.01)
*C08L 13/02* (2006.01)
*B29K 83/00* (2006.01)
*B29L 31/48* (2006.01)

(52) U.S. Cl.
CPC ............... *B29C 41/14* (2013.01); *B29C 41/46* (2013.01); *C08J 3/26* (2013.01); *C08J 5/02* (2013.01); *C08L 13/02* (2013.01); *B29K 2083/00* (2013.01); *B29L 2031/4864* (2013.01); *C08J 2307/02* (2013.01); *C08J 2309/04* (2013.01); *C08J 2309/10* (2013.01); *C08J 2313/02* (2013.01); *C08L 2312/08* (2013.01)

(56) References Cited

U.S. PATENT DOCUMENTS

| | | | | |
|---|---|---|---|---|
| 6,641,879 | B1* | 11/2003 | Matsuura | B29C 37/0067 2/161.7 |
| 8,044,138 | B2* | 10/2011 | Han | C08L 19/006 524/556 |
| 8,389,620 | B2* | 3/2013 | Koide | C08K 3/22 524/457 |
| 8,673,993 | B2 | 3/2014 | Holzner et al. | |
| 8,975,351 | B2* | 3/2015 | Kim | C08F 236/12 526/297 |
| 9,243,117 | B2 | 1/2016 | Khoo et al. | |
| 9,279,038 | B2 | 3/2016 | Schaller et al. | |
| 9,290,632 | B2 | 3/2016 | Holzner et al. | |
| 9,894,946 | B2 | 2/2018 | Holzner et al. | |
| 2003/0118761 | A1* | 6/2003 | Triebes | A61L 31/048 428/35.7 |
| 2005/0113527 | A1* | 5/2005 | Perrella | C08K 5/17 525/310 |
| 2006/0074185 | A1 | 4/2006 | Ganapathiappan et al. | |
| 2008/0227913 | A1* | 9/2008 | Koide | C08K 3/22 525/54.3 |
| 2009/0292081 | A1* | 11/2009 | Suddaby | C08J 3/24 525/370 |
| 2010/0152365 | A1 | 6/2010 | Han et al. | |
| 2011/0289655 | A1 | 12/2011 | Schaller | |
| 2014/0096307 | A1 | 4/2014 | Holzner et al. | |
| 2014/0096308 | A1 | 4/2014 | Holzner et al. | |
| 2017/0099889 | A1* | 4/2017 | Liou | C08F 236/12 |

FOREIGN PATENT DOCUMENTS

| | | | |
|---|---|---|---|
| EP | 2 389 820 | A1 | 11/2011 |
| EP | 2 719 710 | A1 | 4/2014 |
| EP | 2 719 720 | A1 | 4/2014 |
| GB | 1 074 179 | A | 6/1967 |
| WO | 00/11980 | A1 | 3/2000 |
| WO | 2010/105283 | A1 | 9/2010 |
| WO | 2011/068394 | A1 | 6/2011 |
| WO | WO-2016013666 | A1 * | 1/2016 ............ A41D 19/015 |

OTHER PUBLICATIONS

G. N. Onyeagoro "Reactive Compatibilization of Natural Rubber (NR)/Carboxylated Nitrile Rubber (XNBR) Blends by Maleic Anhydride-Grafted-Polyisoprene (MAPI) and Epoxy Resin Dual Compatibilizers" International Refereed Journal of Engineering and Science (IRJES), 2013, 2(3), 7-16. (Year: 2013).*
Pietrasik et al. "Studies of molecular dynamics of carboxylated acrylonitrile-butadiene rubber composites containing in situ synthesized silica particles" European Polymer Journal, 2009, 45, 3317-3325. (Year: 2009).*
Machine translation of WO 2016/013666, translation generated Jan. 2020, 40 pages. (Year: 2020).*
Universität Bayreuth: "Clay and Clay Minerals: Hectorite Festkörperpraktrikum Modul AC III 2014", Jan. 2014 (Jan. 1, 2014), XP055389066, Retrieved from the Internet: URL: http://www.acl.uni-bayreuth.de/de/teaching/downloads/Ton_and_Tonminerale_Hectorit_english.pdf.
DIN 55672-3, Gel permeation chromatography (GPC)—Part 3: Water as eluent, Aug. 2007, pp. 1-27.
DIN 51562-1, Determination of kinematic viscosity using the Ubbelohde viscometer, Part 1: Apparatus and measurement procedure, Jan. 1999, pp. 1-10.
Valentín et al, Uncertainties in the Determination of Cross-Link Density by Equilibrium Swelling Experiments in Natural Rubber, Macromolecules 2008, 41, pp. 4717-4729.
Zaborski et al., Silica Modified by use of Organosilanes as a Filler for Carboxylated Butadiene-Acrylonitrile Rubber, KGK Kautschuk Gummi Kunststoffe 58, 2005, pp. 354-357.
ASTM Standard D 412-98a, "Standard Test Methods for Vulcanized Rubber and Thermoplastic Elastomers-Tension," (Reapproved 2002), pp. 1-14.
International Search Report of PCT/AT2017/060052, dated Jul. 17, 2017.
International Search Report of PCT/AT2017/060053, dated Jul. 12, 2017.
H. Mohd. Ghazaly et al., "Some Factors Affecting Dipped Nitrile Latex Films", J. Rubb. Res., 4(2), 88-101 (2001).
Siriyong et al., "Utilization of Different Curing Systems and Natural Zeolite as Filler and Absorbent for Natural Rubber/Nitrile Rubber Blend", Kasetsart J. (Nat. Sci.) 46 : 918-930 (2012).
Amornchaiyapitak et al., "Modification of epoxidised natural rubber film surface by polymerisation of methyl methacrylate", European Polymer Journal 44 (2008) 1782-1788.
Lenko et al., "Dual Crosslinking of Carboxylated Nitrile Butadiene Rubber Latex Employing the Thiol-ene Photoreaction", Journal of Applied Polymer Science (2013) 2735-2743.
Schloegl et al., "Photo-vulcanization using thiol-ene chemistry: Film formation, morphology and network characerisitcs of UV crosslinked rubber latices", Polymer 55 (Jun. 10, 2014) 5584-5595.
Letter from the Austrian Patent Attorney to the European Patent Office in PCT/AT2017/060053, dated Apr. 12, 2018, with English translation of relevant parts.
Letter from the Austrian Patent Attorney to the European Patent Office in PCT/AT2017/060052, dated Apr. 11, 2018, with English translation of relevant parts.
Brown, H. P., "Crosslinking Reactions of Carboxylic Elastomers", Rubber Chemistry and Technology, Rubber Division, U.S. vol. 36, No. 4, 1963, pp. 931-962, XP001109664, ISSN: 0035-9475.

* cited by examiner

METHOD FOR PRODUCING A PROPHYLACTIC ARTICLE

CROSS REFERENCE TO RELATED APPLICATIONS

This application is the National Stage of PCT/AT2017/060053 filed on Mar. 2, 2017, which claims priority under 35 U.S.C. § 119 of Austrian Application No. A 50176/2016 filed on Mar. 4, 2016, the disclosure of which is incorporated by reference. The international application under PCT article 21(2) was not published in English.

The invention relates to a method for the manufacture of a prophylactic article, especially of a glove, from a (carboxylated) diene rubber, according to which at least one layer of a (carboxylated) diene latex is applied on a former and the (carboxylated) diene latex is cross-linked with a cross-linking agent.

Furthermore, the invention relates to a prophylactic article, especially glove, comprising a layer of a (carboxylated) diene elastomer, wherein the (carboxylated) diene elastomer molecular chains of the (carboxylated) diene elastomer are cross-linked covalently via at least one polymer.

In addition, the invention relates to the use of a multifunctional monomer and/or polymer.

Prophylactic articles, such as surgical and examination gloves in particular, are usually manufactured from an elastomer latex by dipping of hand-shaped dipping formers. A film from which the finished disposable glove is subsequently obtained by vulcanization or cross-linking of the latex is formed on the dipping formers.

Prophylactic articles of natural latex have a relatively high allergy potential. For this reason, synthetic latices are being increasingly used for the manufacture of the prophylactic articles. However, even these are not entirely hypoallergenic, since they may still contain allergens from the manufacturing process, such as powder for improvement of the ability to be slipped on, for example, or process chemicals, such as cross-linking chemicals or cross-linking accelerators, for example.

In order to counter these problems, methods for the manufacture of prophylactic articles with reduced allergy potential have already been proposed in the prior art.

For example, WO 2011/068394 A1 describes a method according to which a methacrylic acid and ZnO are added to a carboxylated nitrile butadiene. Thereby self-cross-linking properties are imparted to this mixture, and so it is possible to dispense with sulfur cross-linkers and accelerators. As in the past, however, this composition still contains the heavy metal Zn, and so a certain allergy potential remains.

Similarly to this, US 2010/0152365 A1 describes the use of a carboxylated nitrile butadiene copolymer for the manufacture of a glove by means of dipping methods. Once again, ZnO is used for ionic cross-linking.

It is further known to modify the surface of natural rubber gloves in order to reduce their allergy potential. Thus US 2014/0096307 A1, for example, originating from the Applicant, describes a method for modification of the surface of an elastomer with unsaturated carbon-carbon bonds, which become saturated in the region of the surface at least partly by a photochemical reaction with at least one thiol. Solid particles that are bound covalently on the surface of the glove may be used for saturation.

Similarly to this, US 2014/0096308 A1, likewise attributed to the Applicant, describes among other aspects the binding of zeolite particles to a natural rubber glove via epoxy groups.

The task underlying the present invention is to create an improved prophylactic article.

In the method cited in the introduction, the task is accomplished by the fact that a multifunctional monomer and/or polymer is used as cross-linking agent, which is added to the (carboxylated) diene latex and dissolved therein or emulsified or dispersed therein.

Furthermore, the task is accomplished by the prophylactic article mentioned in the introduction, in which the at least one polymer is a mercapto-functional siloxane polymer.

The task of the invention is also accomplished by the use of a multifunctional polymer having a number of monomer units between 2 and 50 (a molar mass between 170 g/mol and 4000 g/mol) for adjustment of the modulus of a prophylactic article comprising a (carboxylated) diene elastomer.

In addition, the task of the invention is accomplished by the use of a multifunctional organic compound as cross-linking agent for the manufacture of a prophylactic article, wherein the multifunctional organic compound has a molar mass between 170 g/mol and 4000 g/mol and at least two functional groups, and which forms hydroxy groups under base catalysis.

In this connection, it is of advantage that the cross-linking agent is incorporated better in the cross-linked elastomer due to the chemical reaction of the cross-linking agent with the elastomer molecules. Thereby the cross-linking agent can be extracted not at all or with difficulty from the elastomer and migrates not at all and only very slowly out of the elastomer. In this connection, "very slowly" means that the migration time is very much longer than the duration of use of the prophylactic article. In this way the cross-linking agent is prevented from coming into contact with the human skin, whereby the allergy potential of the prophylactic article can be significantly reduced. Even during the storage of the prophylactic article, the migration of the cross-linking agent out of the prophylactic article can be prevented or significantly reduced. In addition, leaching processes for removal of unbound process chemicals can thereby be shortened or even omitted. The cross-linking agent may be a multifunctional monomer and/or polymer or mixtures thereof. With the method, it is possible to manufacture a prophylactic article that has very good mechanical properties and high aging and gamma resistance. Even an influence on the film formation during the manufacturing process, especially the dipping process, has not been proved, and so no further measures are needed in that respect. A further advantage of the method can be seen in the fact that no preliminary cross-linking of the (carboxylated) diene latex is necessary, and so continuous mixing methods may be used and the process workflows can be accelerated. With the method, an energy-efficient, sustainable and production-efficient manufacture of hypoallergenic prophylactic articles is possible, especially of surgical and examination gloves. Due to the water solubility of the cross-linking agent, an emulsifier is not or not necessarily needed for its introduction into the latex mixture. The multifunctional monomers and/or polymers have the advantage of simpler handling, since the soluble monomer and/or polymer can be mixed into the latex without prior dispersion or emulsion. The intermixing in the form of an emulsion is possible, however, especially in the case of oil-soluble monomers and/or oil-soluble polymers. In addition, the modulus of the prophylactic article can also be better adjusted.

According to a preferred embodiment variant of the method, it may be provided that exclusively the multifunctional monomer and/or polymer is used as cross-linking agent. In this way the effects cited in the foregoing can be further improved, wherein it may be additionally achieved that, by the omission of heavy metal ions, such as $Zn^{2+}$ from ZnO, for example, the allergy potential can be further reduced (as an example, zinc can be extracted from the elastomer with carboxylic acids, such as acetic acid, for example). Beyond this, no influence of another cross-linking system can occur, as is sometimes reported in the prior art.

The cross-linking of the (carboxylated) diene latex molecules can be achieved thermally. Thus the cross-linking of the latex molecules can already take place during the drying of the latex film dipping-applied onto the dipping former, whereby an increase of efficiency of the method is achievable.

It is further possible to carry out the cross-linking of the (carboxylated) diene latex molecules photochemically by means of UV light. In this way, the aging resistance of the elastomer can be improved. The elastomer products also exhibit an improved stability with respect to high-energy radiation. This is of importance especially with respect to the sterilization of the medical devices with gamma radiation. In addition, the use of type IV allergenic substances may likewise be avoided more easily due to this method.

Preferably, the pH of the (carboxylated) diene latex is adjusted to a value of greater than/equal to 9. A distinct improvement of the reaction kinetics has been observed with pH values of 9 or higher, whereby the cross-linking of the molecules is able to take place more rapidly.

The cross-linking agent may be selected from a group consisting of multifunctional epoxides, multifunctional silanes, multifunctional siloxanes, multifunctional thiols. In this connection, it is of advantage when these (i) have more than one epoxy function for the cross-linking of the rubber chains. Preferably, the multifunctional epoxides have a structure that the hydrolysis product has "nurturing" properties, such as, for example diglycidyl-terminated polyethylene glycol derivative, epoxy-sorbitol derivative, derivative of a sugar alcohol. Furthermore, it is possible to use, for example, monosaccharides and polysaccharides with epoxy functionalities.

In carboxylated diene latices, the cross-linking with epoxides offers the advantage that covalent network sites are formed via the carboxyl groups and thereby very high tear strengths result—in contrast, the covalent cross-linking via the C═C double bonds of the butadiene units achieve hardly any improvement in the strengths.

A further advantage of epoxides is the high reactivity with carboxyl groups (no additional accelerator or initiator is needed), which leads to an efficient cross-linking during the drying step.

It is of advantage for the multifunctional thiols when they (i) have a high molar mass (molar mass between 200 g/mol and 4000 g/mol); (ii) a high mercapto equivalent number (at least 20%, especially at least 50% of the monomer units should carry SH— groups); (iii) are accessible via simple synthesis strategies. On the basis of the high molecular weight, even odor problems can be handled more effectively.

It is of advantage for the multifunctional silanes and siloxanes when they (i) carry more than one reactive group (e.g. CoatOSil MP200 leads to higher tear strengths than 3-glycidoxypropyltrimethoxysilane). In this connection, it is further of advantage that these are still liquid even at high molar masses (e.g. up to 4000 g/mol) and thereby can be introduced more easily into the latex mixture. Beyond this, an excessively large increase of the modulus can be avoided with the siloxanes, due to their flexible backbone.

For better adjustment of the modulus of the prophylactic article, it may be provided that an organic monomer and/or polymer is used that has a molar mass between 170 g/mol and 4000 g/mol. In this way, a better wearing comfort can be achieved for the user of the prophylactic article.

As already stated, the possibility also exists of adding the cross-linking agent as emulsion to the (carboxylated) diene latex. This is of advantage in particular when the mercapto-functional siloxane polymer is used as cross-linking agent. Due to the fine distribution of the cross-linking agent in the emulsion, a more homogeneous prophylactic article can be obtained more simply.

According to one embodiment variant, a mercapto-functional siloxane homopolymer or a copolymer of the mercapto-functional siloxane homopolymer with an acrylic siloxane may be used as the mercapto-functional siloxane polymer. In the course of conducted tests, these polymers have already proved positive, at low concentrations, for the mechanical properties of the prophylactic article cross-linked therewith.

Particularly preferably, according to one embodiment variant of the method, a mercapto-functional siloxane homopolymer with the structural formula

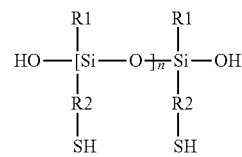

is used, wherein R1 stands for a first unit selected from a first group consisting of —CH$_3$, —OH, —C$_2$H$_5$, —C$_3$H$_7$, aromatic groups, R2 for a second unit selected from a second group consisting of —CH$_2$, C$_2$H$_4$, C$_3$H$_6$; —(CH$_2$)$_{11}$—, aromatic groups, —CH$_2$— aromatic. Likewise particularly preferably, according to a further embodiment variant of the method, a mercapto-functional siloxane copolymer, especially a mercapto-functional siloxane copolymer with a statistical arrangement of the repeat units, with the structural formula

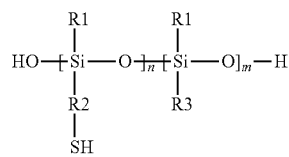

is used, wherein R1 stands for a first unit selected from a first group consisting of —CH$_3$, —OH, —C$_2$H$_5$, —C$_3$H$_7$, aromatic groups, R2 for a second unit selected from a second group consisting of —CH$_2$, C$_2$H$_4$, C$_3$H$_6$; —(CH$_2$)$_{11}$—, aromatic groups, —CH$_2$— aromatic, and R3 for a third unit, selected from a third group consisting of alkyl groups (—CH$_3$, —C$_2$H$_5$, —C$_3$H$_7$, etc.), —CH$_2$— aromatic, aromatic groups, alkene groups (—CH═CH$_2$, —CH$_2$CH═CH$_2$, etc.), methacryloxypropyl-, acryloxypropyl-, epoxy groups (epoxycyclohexylethyl, glycidoxypropyl). The effects mentioned in the foregoing can be further improved by these polymers.

The dimer below may also be used as the mercaptofunctional siloxane.

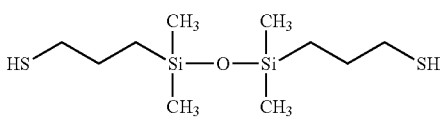

In the course of studies in connection with this invention, it was found that it is of advantage when the mercaptofunctional siloxane homopolymer is selected from a group consisting of poly(mercaptopropyl) siloxane, poly(mercaptomethylpropyl) siloxane, poly(mercaptomethylmethyl) siloxane, poly(mercaptoethylmethyl) siloxane, poly(mercaptomethylethyl) siloxane, poly(mercaptopropylmethyl) siloxane, poly(mercaptomethylbenzyl) siloxane, poly(mercaptopropylbenzyl) siloxane, poly(mercaptoethylbenzyl) siloxane and/or the copolymer of the mercapto-functional siloxane homopolymer with an acrylic siloxane selected from a group consisting of poly(mercaptomethylpropyl-co-acryloxymethylpropyl) siloxane, poly(mercaptomethylmethyl-co-acryloxymethylpropyl) siloxane, poly(mercaptomethylmethyl-co-acryloxypropylmethyl) siloxane, poly(mercaptomethylmethyl-co-acryloxypropylethyl) siloxane, poly(mercaptomethylmethyl-co-acryloxyethylpropyl) siloxane, poly(mercaptomethylmethyl-co-acryloxymethylmethyl) siloxane, poly(mercaptomethylmethyl-co-acryloxypropyl) siloxane, poly(mercaptomethylmethyl-co-acryloxyethyl) siloxane, poly(mercaptomethylmethyl-co-acryloxymethyl) siloxane, poly(mercaptopropylmethyl-co-acryloxymethylpropyl) siloxane. In this connection, it is of advantage that these compounds have a high mercapto equivalent number and thus a high reactivity for the cross-linking. In addition, they are liquid and thus can be introduced simply into the system via emulsion. Beyond this, they are odorless and even in high concentration do not influence the film formation. Due to the polar character of the SH groups, the emulsions are also stable over prolonged time.

Due to the acrylate groups, on the one hand disulfide formation (via neighboring units) is prevented from occurring repeatedly during the UV cross-linking, and on the other hand the acrylate group is likewise capable of reacting with the rubber in the course of the thiol-ene reaction.

According to a further embodiment variant of the method, it may be provided that the proportion of mercapto-functional siloxane polymer in the copolymer of the mercapto-functional siloxane polymer with an acrylic siloxane is at least 20 wt %. In this way the advantages/effects mentioned in the foregoing can be better achieved.

The cross-linking agent may be added to the (carboxylated) diene latex in a proportion of 1 phr to 10 phr relative to the total composition of the (carboxylated) diene latex. In this way, the 50% modulus can be prevented better from becoming too high, whereby the load-bearing ability of the prophylactic article would suffer. At the same time, however, good mechanical further properties of the elastomer, such as the tear strength or the maximum extensibility, for example, are obtained with a concentration of the cross-linking agent from this range. Preferably, at least one photoinitiator is also added in a proportion of 0.5 phr to 5 phr. Especially α-hydroxyalkylphenones, α-aminoalkylphenones, acyl-phosphine oxides, benzoin ethers, benzil ketals, α-dialkoxy-acetophenones may be used as photoinitiators.

For better understanding of the invention, it will be explained in more detail on the basis of the following figures, wherein.

Figure 1:
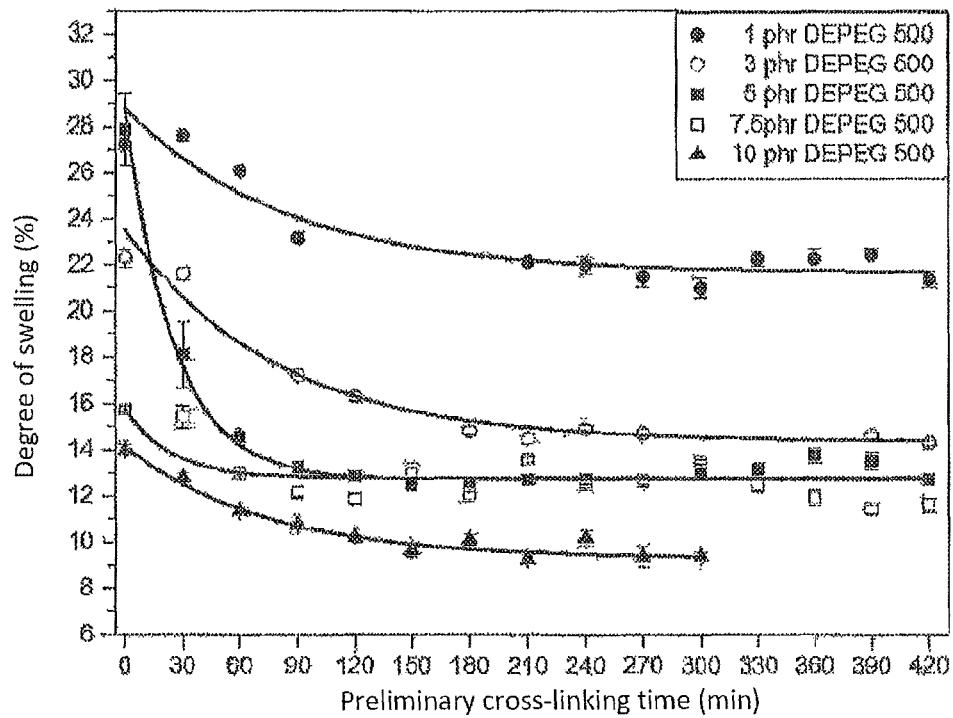
FIG. 1 shows the degree of swelling of cross-linked XNBR latex films versus the cross-linking time at different DEPEG-500 concentrations.

All standards cited in the description refer to the version in force on the date of application of the subject patent application, unless otherwise indicated.

The invention relates to a method for the manufacture of a prophylactic article.

The prophylactic article is preferably a glove, especially a surgical glove (glove for operations) or an examination glove. However, the prophylactic article may also be, for example, a finger stall, a catheter, a condom, a (medical) balloon, a teat, etc. In general, the prophylactic article is preferably a dipped article, i.e. a product that is manufactured by means of a dipping method.

In the following, only the formation of the prophylactic article as a glove will be discussed further. Nevertheless, the explanations in this regard may also be applied to other elastomer articles, especially dipped articles that are manufactured according to a dipping method.

The glove comprises a diene elastomer (diene rubber), especially a carboxylated diene elastomer, or consists of the same.

The elastomer of the elastomer layer may be based both on a natural latex and on a synthetic latex. These may be selected from a group comprising or consisting of natural rubber (NR), polyisoprene latex (IR), nitrile butadiene rubber latex (NBR), carboxylated nitrile butadiene rubber latex (XNBR), carboxylated butadiene latex (XBR), chloroprene latex (CR), styrene-butadiene latex (SBR), carboxylated latices prepared from polymer blends and mixtures thereof.

In particular, a carboxylated nitrile butadiene rubber latex or a polyisoprene latex or a natural rubber is used for the manufacture of the elastomer layer. The nitrile butadiene rubber latex preferably has a proportion of acrylonitrile between 15 wt % and 40 wt %, especially between 20 wt % and 35 wt %.

The prophylactic article or the elastomer glove is preferably manufactured according to a dipping method. Such dipping methods are known in principle from the prior art, and so the pertinent prior art should be consulted for details in this respect.

In this method, essentially a dipping former (in the series fabrication, usually several dipping formers are used) is dipped into a dipping bath. This dipping former has the shape of the finished product, i.e. the shape of a hand, for example.

The respective elastomer latex to be dipping-applied onto the dipping former is introduced beforehand into the dipping bath.

In principle, however, any other suitable shape may be used in the method presented in this description, especially when the elastomer layer is not manufactured according to the dipping method. The elastomer layer may also be prepared by brushing or spraying the elastomer latex onto a former. Likewise, other suitable methods of application of the latex onto a former are applicable.

In this description, the term elastomer latex is used in a way corresponding to usual practice in the language of the art. Accordingly, an elastomer latex is a dispersion of polymer molecules that are non-cross-linked or preliminarily cross-linked or can be cross-linked for the preparation of an elastomer. Within the scope of the invention, therefore, preliminarily cross-linked elastomer latices may also be processed, wherein the preliminary cross-linking may be achieved in particular by means of the cross-linking agent, cited in this description, which is a multifunctional monomer and/or polymer that is added to the (carboxylated) diene latex and dissolved therein or emulsified or dispersed therein.

It is further possible, however, that the elastomer latex is cross-linked only after the application onto the former, i.e. the applied elastomer matrix.

A customary process route of a coagulant dipping method may comprise, for example, the following method steps:
  washing of the dipping former and degreasing with an organic solvent;
  preheating the dipping former;
  dipping the dipping former into a first dipping bath containing a coagulant;
  drying of the first dipping-applied layer;
  dipping of the dipping former into a further dipping bath for formation of the elastomer layer;
  drying/vulcanization (cross-linking);
  pulling the dipped article off from the former.

As is explained in more detail in the following, a photochemical cross-linking by means of UV light, if necessary after addition of a photoinitiator, may be carried out instead of the thermal cross-linking of the elastomer molecules. The photoinitiator may be a commercial photoinitiator and be added in customary concentrations. In this regard, reference is made to US 2014/0096307 A1 and US 2014/0096308 A1, which are cited in the introduction and which, as regards the scope of the photoinitiators and their concentrations in the latex, belong to the subject description.

For the case that the elastomer glove is formed in multiple-layer manner, further layers of the first elastomer latex or of another elastomer latex or of another polymer may be dipping-applied or generally applied. For example, a polymer layer may be dipping-applied as the last layer which, after the pulling of the glove off from the dipping former, becomes disposed on the inside of the glove after the turning of the glove inside out that takes place in the process. Such polymer layers may be formed, for example, as sliding layers, in order to improve the ability of the elastomer glove to be pulled off.

Thus the elastomer glove may be formed in single-layer or multiple-layer manner, wherein the individual layers may consist of materials that are different from one another or of the same materials. It is also possible that two or more layers of the elastomer glove consist of the same material and one or more layers consist of a material different from those.

Since all this is inherently known, it will not be further discussed.

As used in this description, materials will be understood as elastomers and polymers, but the elastomer glove will have at least one layer of an elastomer.

The terms vulcanization and cross-linking will be used synonymously in this description.

For cross-linking of the (carboxylated) diene elastomer latex, a cross-linking agent will be added thereto, i.e. especially to the dipping bath for the manufacture of the at least one layer of the (carboxylated) diene elastomer. In addition, the diene elastomer latex or the dipping bath may contain at least one further additive, such as, for example, at least one emulsifier, at least one antioxidant, at least one dye, at least one anti-ozonant, such as are inherently known for the manufacture of dipped articles. The total proportion of these additives may amount to between 0.1 phr and 10 phr relative to the total composition of the diene elastomer latex or of the dipping bath.

A cross-linking agent on monomeric and/or polymeric basis is added to the (carboxylated) diene elastomer latex and dissolved in the (carboxylated) diene elastomer latex. The concentrations of cross-linking agent may be between 1 phr and 15 phr, especially between 1 phr and 7.5 phr.

In the preferred embodiment variant of the method, no further cross-linking agents are used, i.e. exclusively the monomer and/or polymer soluble in the (carboxylated) diene elastomer latex is used as cross-linking agent. However, as already explained in the foregoing, at least one photoinitiator may be added.

In this connection, the term "polymer" in the sense of this description generally comprises molecules with two or more monomer units, i.e. molecules from dimers up. The multifunctional monomers and/or polymers are preferably selected from a group comprising or consisting of multifunctional epoxide(s), multifunctional silane(s), multifunctional siloxane(s), multifunctional thiol(s), as well as mixtures thereof.

Examples of these are short-chain: sorbitol polyglycidyl ether, glycerol glycidyl ether, 1,6-hexanediol diglycidyl ether, resorcinol diglycidyl ether, 1,4-cyclohexanedimethanol diglycidyl ether, diglycidyl 1,2-cyclohexanedicarboxylate; long-chain: diepoxy-terminated polyethylene glycol, diepoxy-terminated polypropylene glycol, polyglycidyl methacrylate (homopolymers and copolymers with ethylene glycol units, ethylene units, etc.), polyglycerine polyglycidyl ether, polyglycidoxypropyltrimethoxysilane.

Short-chain compounds are monomeric multifunctional compounds, especially such compounds with a molar mass of at least 170 g/mol. Long-chain compounds have at least two or more repeat units (dimers and higher).

Within the scope of the invention, the term "polymer" generally also comprises oligomers.

According to another embodiment variant of the method, it may be provided that a mercapto-functional siloxane homopolymer or a copolymer of the mercapto-functional siloxane homopolymer with an acrylic siloxane is used as the mercapto-functional siloxane polymer. In particular, a mercapto-functional siloxane homopolymer with the structural formula

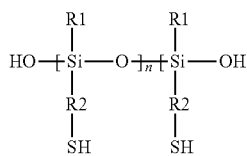

is used, wherein R1 stands for a first unit selected from a first group consisting of —$CH_3$, —OH, —$C_2H_5$, —$C_3H_7$, aromatic groups, R2 for a second unit selected from a second group consisting of —$CH_2$, $C_2H_4$, $C_3H_6$; —$(CH_2)_{11}$, aromatic groups, —$CH_2$— aromatic, and/or an acrylic siloxane with the structural formula

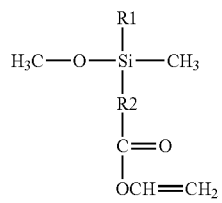

is used, wherein R1 stands for a first unit selected from a first group consisting of —OH, —$CH_3$, —$C_2H_5$, —$C_3H_7$, aromatic groups, R2 for a second unit selected from a second group consisting of —$CH_2$, $C_2H_4$, $C_3H_6$; aromatic groups.

The dimer below may also be used as the mercapto-functional siloxane.

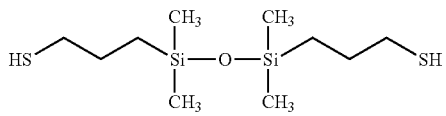

According to a particularly preferred embodiment variant of the method, the mercapto-functional siloxane homopolymer is selected from a group consisting of poly(mercaptomethylpropyl) siloxane, poly(mercaptomethylpropyl) siloxane, poly(mercaptomethylmethyl) siloxane, poly(mercaptoethylmethyl) siloxane, poly(mercaptomethylethyl) siloxane, poly(mercaptopropylmethyl) siloxane, poly(mercaptomethylbenzyl) siloxane, poly(mercaptopropylbenzyl) siloxane, poly(mercaptoethylbenzyl) siloxane and/or the copolymer of the mercapto-functional siloxane homopolymer with an acrylic siloxane is selected from a group consisting of poly(mercaptomethylpropyl-co-acryloxymethylpropyl) siloxane, poly(mercaptomethylmethyl-co-acryloxymethylpropyl) siloxane, poly(mercaptomethylmethyl-co-acryloxypropylmethyl) siloxane, poly(mercaptomethylmethyl-co-acryloxypropylethyl) siloxane, poly(mercaptomethylmethyl-co-acryloxyethylpropyl) siloxane, poly(mercaptomethylmethyl-co-acryloxymethylmethyl) siloxane, poly(mercaptomethylmethyl-co-acryloxypropyl) siloxane, poly(mercaptomethylmethyl-co-acryloxyethyl) siloxane, poly(mercaptomethylmethyl-co-acryloxymethyl) siloxane, poly(mercaptopropylmethyl-co-acryloxymethylpropyl) siloxane.

The proportion of the mercapto-functional siloxane polymer in the copolymer of the mercapto-functional siloxane polymer with an acrylic siloxane may be selected from a range of 20 wt % to 99 wt %, especially from a range of 20 wt % to 80 wt %.

The layer thickness of the elastomer layer may amount to between 30 μm and 500 μm.

In general, the (carboxylated) diene elastomer latex can have a solids content of (carboxylated) diene elastomer between 10 drc (dry rubber content) and 60 drc.

It is further of advantage when the pH of the (carboxylated) diene elastomer latex is adjusted to a value of greater than/equal to 9. As an example, an aqueous KOH solution (1 wt % to 5 wt %) may be used for this purpose. In general, suitable basic substances, such as lyes, may be used for this purpose.

In a preferred embodiment variant of the method, the cross-linking of the (carboxylated) diene elastomer molecules is carried out thermally, especially during the drying of the (dipping-applied) layer of the (carboxylated) diene elastomer latex. In the process, the temperature may be between 90° C. and 140° C. The cross-linking may take place during a time span between 5 minutes and 20 minutes.

It is possible to use a cross-linking agent that has a molar mass between 170 g/mol and 4000 g/mol, especially between 170 g/mol and 1700 g/mol (polymeric, water-soluble compounds according to DIN 55672-3:2007-08 (GPC)) or, via the viscosity of liquid polymers, according to DIN 51 562-1). For example, it is possible to use ethylene glycol diglycidyl ether (molar mass 170 g/mol) or diethylene glycol diglycidyl ether (molar mass 218 g/mol). In this way it is also possible to adjust the (50%) modulus of the elastomer glove to a desired value. The modulus of the elastomer glove may be adjusted via the chain length of the cross-linking agent.

With the method, a prophylactic article, especially glove, may be manufactured comprising a layer of a (carboxylated) diene elastomer, wherein the (carboxylated) diene elastomer molecular chains of the (carboxylated) diene elastomer are cross-linked covalently via organic molecules.

The elastomer gloves manufactured according to the method exhibit a good skin tolerability. On the basis of conducted investigations, no skin irritation and no sensitization potential have been observed.

In the course of the testing of the cross-linking method, the following experiments among others were conducted. These are merely selected examples, since the reproduction of all experiments would go beyond the scope of this description.

In the following, the experimental results are presented for the performance of the method with multifunctional monomers and/or polymers as cross-linking agents. The reagents used for this purpose are summarized in Table 1.

TABLE 1

Materials used

| Name | Function | Description |
| --- | --- | --- |
| Nipol LX556 ZEON Corporation (JPN) BST8502N PolyLac 582N | Latex | 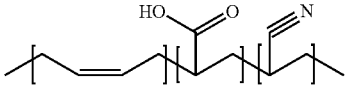 XNBR Dry rubber content: 45.2% pH: 8 to 8.8 |
| SPE, sorbitol polyglycidyl ether CVC Thermo-set Specialities | Polymeric cross-linking agent | 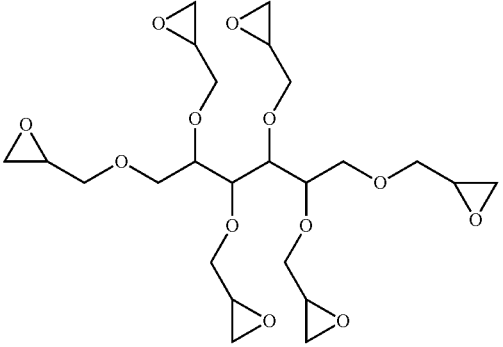 [SMILES: C(OCC(OCC1CO1)C(OCC1CO1)C(OCC1CO1)C(COCC1CO1)OCC1CO1)C1CO1] Sorbitol polyglycidyl ether (ERISYS GE 60) |
| GE100 Raschig | Polymeric cross-linking agent | 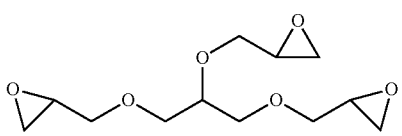 [SMILES: C(OCC1CO1)C(COCC1CO1)OCC1CO1] Glycerol glycidyl ether |
| DEPEG Sigma-Aldrich (USA) PolyScience (USA) | Polymeric cross-linking agent | 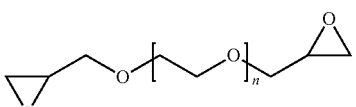 Diepoxy-terminated polyethylene glycol DEPEG-200 Mn = 200 DEPEG-500 Mn = 500 DEPEG-1000 Mn = 1000 |

Preparation of the Latex Mixtures, Dipping and Cross-Linking

The water-soluble cross-linking agent was added in different concentration (0.5 to 1.5 phr) to the latex mixture (pH=10, ~25 drc). The mixture was then doped with an antioxidant (0.5 phr to 2 phr Ralox) and stirred at room temperature for approximately 15 min. Then the films were prepared by means of the coagulant dipping method described in the foregoing and the films were dried at 100° C. for 15 min. No preliminary cross-linking or latex maturing was needed. The cross-linking took place during the drying of the films at 100° C.

The latex mixture can be stirred gently by means of a magnetic stirrer during the dipping process. This applies in general to the method presented in this description.

The following reactions constitute the basis of the thermal cross-linking with monomeric and/or polymeric epoxy cross-linkers. The adjustment of the pH of the latex mixture in advance is of advantage, for example with 1 wt % KOH to pH=10, since the reaction is catalyzed at higher pH values.

Reaction of a Carboxylated Elastomer with an Epoxide

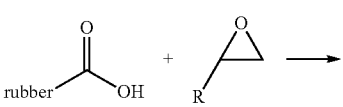

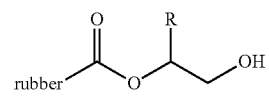

Acid-Catalyzed and Base-Catalyzed Ring Opening of Epoxides.

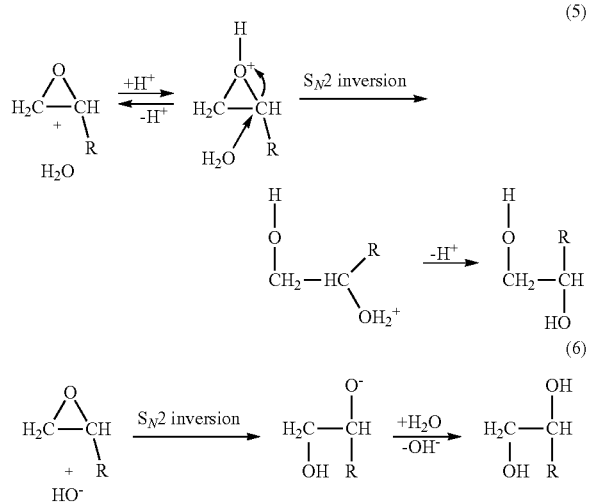

Figure 2:
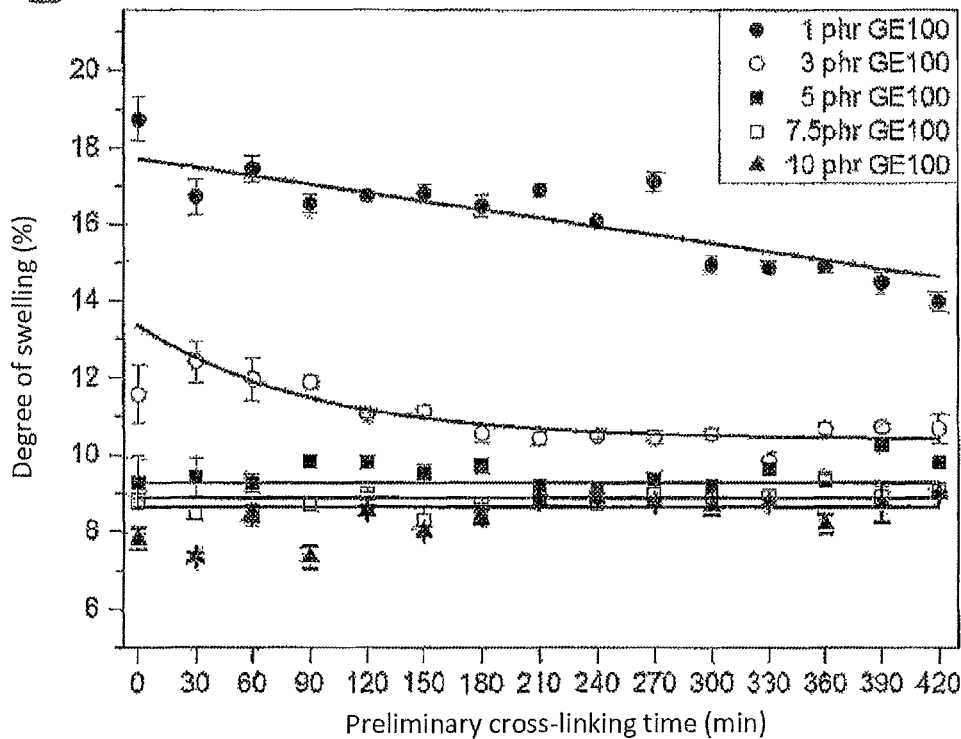
FIG. 2 shows the degree of swelling of cross-linked XNBR latex films versus the cross-linking time at different GE-100 concentrations.
Figure 3:
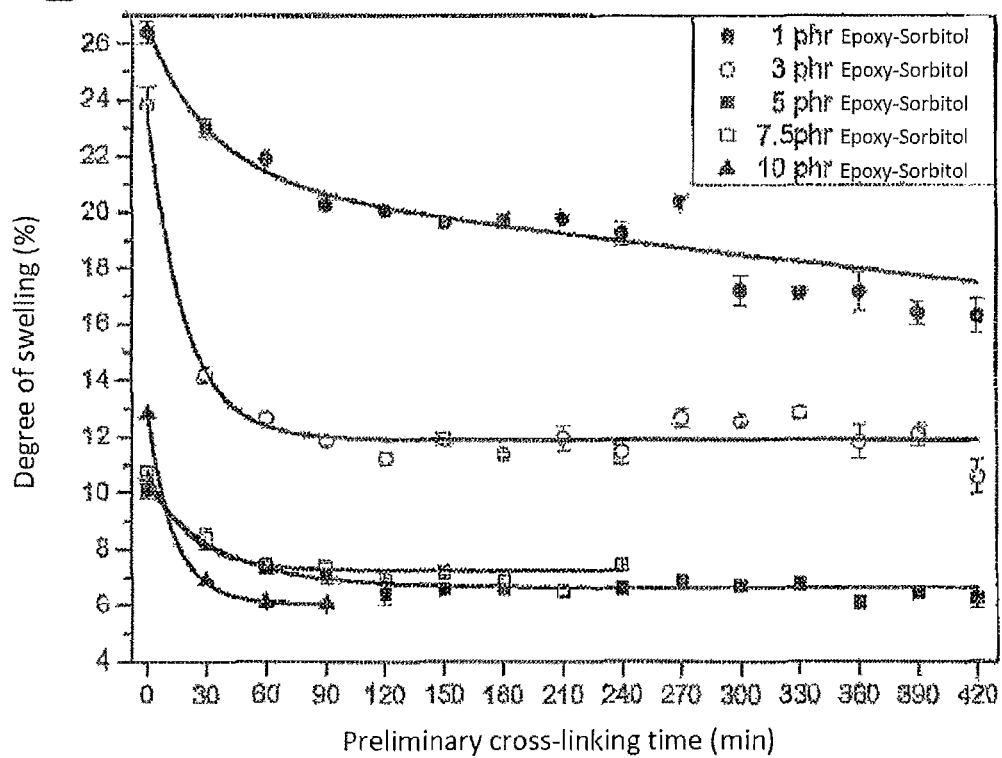
FIG. 3 shows the degree of swelling of cross-linked XNBR latex films versus the cross-linking time at different SPE concentrations.

The successful cross-linking of XNBR latex by addition of selected water-soluble polymeric cross-linking agents was demonstrated by means of equilibrium swelling in chloroform (determined according to: (1) Macromolecules 2008, 41, 4717-4729, (2) J. Appl. Polym. Sci. 129(5), 2735-2743 and (3) Zaborski, M.; Kosmalska, A.; Gulinski, J. Kautsch. Gummi Kunstst. 2005, 58, 354). The results are plotted in FIGS. 1 to 3. In this connection, the cross-linking time in minutes is plotted on the abscissas and the degree of swelling on the ordinates. In this case, the cross-linking density becomes greater with increasing cross-linking time and cross-linking agent concentration, wherein the reactivity of the cross-linking agents increases in the order DEPEG-500<SPE<GE100.

Besides the equilibrium swelling, the cross-linking of XNBR latex by addition of selected water-soluble polymeric cross-linking agents was also demonstrated by means of tension testing.

During use of DEPEG-500, mechanical strengths in the range of 22±2 MPa were observed at a concentration of 5 phr and higher. At lower concentrations (0.5 to 3 phr), a low cross-linking density was achieved and the tear strengths lie below 10 MPa. An increase of the cross-linker concentration to 7.5 phr causes a further increase of the strengths up to 35±2 MPa. Therefore a concentration of 5 phr to 7.5 phr is preferred.

Very good mechanical strengths and aging resistances and gamma resistances were also observed with DEPEG-200 in a concentration range between 3 phr and 7.5 phr (non-sterile/non-aged: 26 MPa-40 MPa; non-sterile/aged: 37 MPa-26 MPa; sterile/non-aged: 28 MPa-24 MPa; sterile/aged: 25 MPa-35 MPa).

Since similar results were also achieved with other multifunctional monomeric and polymeric cross-linking agents, a concentration of 1 phr to 7.5 phr multifunctional monomeric and/or polymeric cross-linking agents in the latex is generally preferred.

Furthermore, an excellent hot-air aging resistance (7 days of storage at 70° C.) and gamma resistance (25 kGy) is observed.

In general, it must be pointed out that, in the course of tests of the prophylactic article, the sterilization can be carried out by gamma irradiation with a Co-60 source and an irradiation dose of 25 kGy. The aging may generally be carried out by hot-air aging at 70° C. for 7 days in the circulating-air oven.

Figure 4:
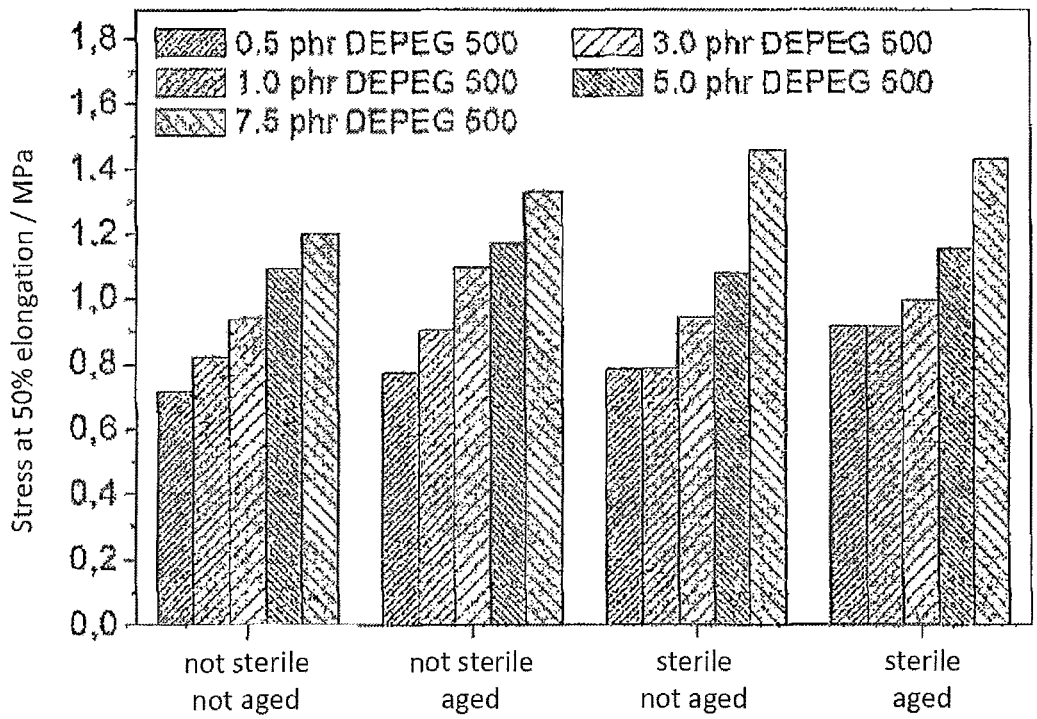
FIG. 4 shows the moduli (50% elongation) of cross-linked XNBR latex films at different DEPEG-500 concentrations.

In addition, the stress value at 50% elongation lies in the range of 1.2 to 1.4 MPa even for high tear strengths and, especially during use of 5 phr cross-linking agent, is hardly increased even after hot-air aging and gamma sterilization. This is of advantage most of all for the manufacture of surgical gloves, since a low stress value at 50% elongation is a criterion for a pleasant wearing comfort. The results of the measurement of the 50% elongation are plotted in FIG. 4. Therein, the bars are arranged in groups of five wherein, within each group of five, the bars stand for a concentration of DEPEG-500, from left to right, of 0.5 phr, 1.0 phr, 3.0 phr, 5.0 phr and 7.5 phr. From left to right, the groups of five themselves stand for non-sterile and non-aged, non-sterile and aged, sterile and non-aged as well as sterile and aged samples. The 50% moduli in MPa are indicated on the ordinate.

Analogously to the cross-linking with DEPEG-500, very good mechanical properties (even after gamma sterilization) were also demonstrated for use of SPE (sorbitol polyglycidyl ether) at higher concentrations (7.5 phr). At a concentration of 7.5 phr SPE, values between 12 MPa and 32 MPa were measured for the mechanical properties (non-sterile/non-aged: 30 MPa-32 MPa; non-sterile/aged: 12 MPa-14 MPa; sterile/non-aged: 30 MPa-32 MPa; sterile/aged: 13 MPa-15 MPa). In contrast, at a concentration of DEPEG-500 between 0.5 phr and 1.0 phr, only values of approximately 5 MPa at maximum were measured. Preferably, therefore, DEPEG-500 is used in a quantity of 5 phr to 7.5 phr.

During use of SPE as a water-soluble polymeric cross-linking agent, a pronounced increase of the stress value at 50% elongation is additionally observed, which is detrimental for the wearing comfort of the elastomer glove. At 7.5 phr SPE, values in the range of 1.6 to 1.8 MPa are obtained. Preferably, therefore, SPE is used in a concentration of 0.5 phr to 5 phr.

During use of GE100 as the cross-linking agent, very good mechanical strengths, which lie in the range of 20 to 27 MPa, are already obtained at low concentrations (1 and 3 phr). With higher cross-linking agent concentrations (7.5 phr), a further increase of the tear strengths is observed (37±2 MPa). At a concentration of 5 phr, values between 22 MPa and 40 MPa were obtained (non-sterile/non-aged: 35 MPa-40 MPa; non-sterile/aged: 32 MPa-35 MPa; sterile/non-aged: 36 MPa-38 MPa; sterile/aged: 22 MPa-23 MPa). The cross-linked XNBR latex films are characterized by a very good gamma resistance.

In summary, it may be concluded from the results that high tear strengths (30±2 MPa) and gamma resistances (after gamma sterilization: 30±2 MPa) were obtained with all three investigated cross-linking agents. As regards resistance to a hot-air aging or a low modulus at 50% elongation, DEPEG-500 exhibits clear advantages compared with GE-100 and SPE.

Based on these results, the modulus value of the cross-linked XNBR latex films was selectively adjusted in further investigations via the molar mass of the epoxy-terminated polyethylene glycol derivative (DEPEG). With low molar mass, a very high strength (up to 40 MPa) is obtained on the one hand, while the modulus increases. This is interesting above all for the manufacture of examination gloves, where high strengths are the main concern and the modulus (on the basis of the layer thickness) plays only a subordinate role.

For XNBR films that were cross-linked with DEPEG-500 (mean molar mass), somewhat lower strengths are indeed obtained, but the modulus values are substantially lower. This variant is suitable more for the manufacture of examination gloves, where the main focus lies on a low modulus.

However, if the molar mass of the cross-linking agent lies in the range of 1,000 g/mol, the 50% modulus value can indeed by brought below 1 MPa, but the corresponding tear strengths also lie below 15 MPa. The results therefore show that a balance between tear strength and modulus may be adjusted via the chain length of the cross-linking agent. The chain lengths of the polymeric cross-linking agents mentioned in the foregoing are therefore preferred.

Figure 5:
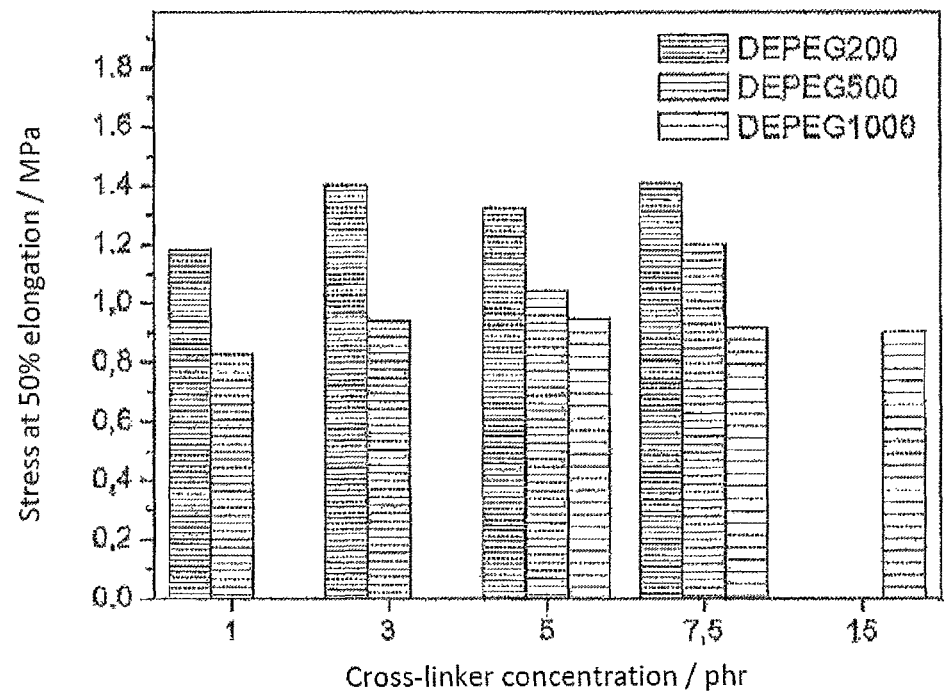
FIG. 5 shows the moduli (50% elongation) of cross-linked XNBR latex films (non-sterile/non-aged) for DEPEG types with different molar mass.
Figure 6:
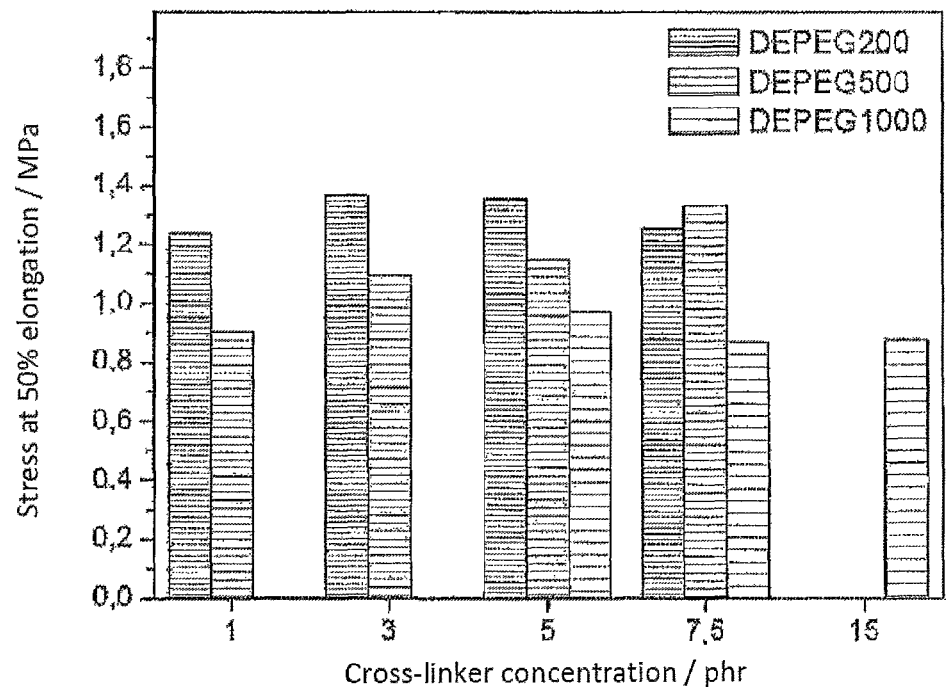
FIG. 6 shows the moduli (50% elongation) of cross-linked XNBR latex films (non-sterile/aged at 70° C. for 7 days) for DEPEG types with different molar mass.

The measured results of this investigation are plotted in FIGS. 5 and 6. Therein the concentration of cross-linking agent in phr is plotted on the abscissas and the measured stresses at 50% elongations in MPa on the ordinates.

In further investigations, PolyLac 582N as a further alternative latex type was cross-linked with 5 phr DEPEG-200 at different pH values. The results show clearly that a successful cross-linking of PolyLac 582N is possible.

In the following, selected examples of the photochemical cross-linking of elastomer latices are presented. The reagents used for this purpose are summarized in Table 2.

TABLE 2

| | | Materials used | |
|---|---|---|---|
| Name | Function | | Description |
| Natural rubber latex | Latex | | NR High ammonia, 60% drc |
| Isoprene rubber latex Kraton | Latex | | 60% drc |
| 3-Mercaptopropyl-trimethoxysilane ABCR | Monomer for synthesis of the polymeric cross linker | | 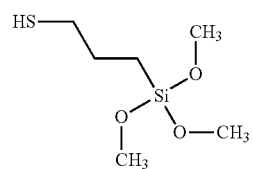 MPTMS |
| 3-Mercaptopropyl-methyldimethoxysilane ABCR | Monomer for synthesis of the polymeric cross linker | | 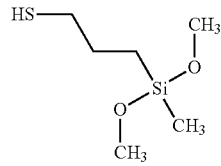 MPMDMS |
| 3-Mercaptomethyl-methyldimethoxysilane ABCR | Monomer for synthesis of the polymeric cross linker | | 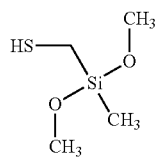 MMMDMS |
| 3-Acryloxypropyl-methyldimethoxysilane ABCR | Monomer for synthesis of the polymeric cross linker | | 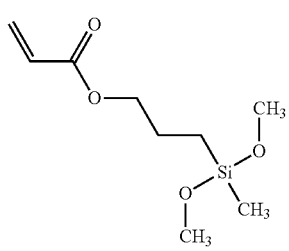 APMDMS |

TABLE 2-continued

Materials used

| Name | Function | Description |
|---|---|---|
| Lucirin TPO-L BASF | Photoinitiator | |
| Tween 20 | Emulsifier | |
| Ionol LC | Antioxidant | |

The preparation of the polymeric siloxane cross-linking agent may be carried out as follows.

0.1 M HCl (aqueous) and ethanol are introduced into a receiver beforehand and heated to 50° C. while a continuous stream of $N_2$ is passed through. Then the corresponding siloxane monomers (see Table 2) are added in selected concentrations of 5% (w/v) and 40% (w/v). After 3 to 9 hours at 50° C., the reaction is stopped by cooling and the oily product is washed with deionized water and extracted with chloroform. The solvent is then drawn off under vacuum, and the product is stored under $N_2$ atmosphere.

The reaction mechanisms of the synthesized homopolymers and copolymers are presented in the following.

Synthesis of Poly(Mercaptopropyl) Siloxane:

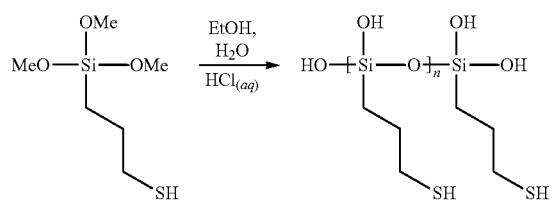

Synthesis of Poly(Mercaptomethylmethyl) Siloxane:

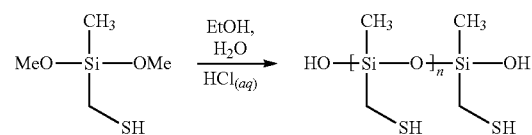

Synthesis of Poly(Mercaptopropylmethyl) Siloxane

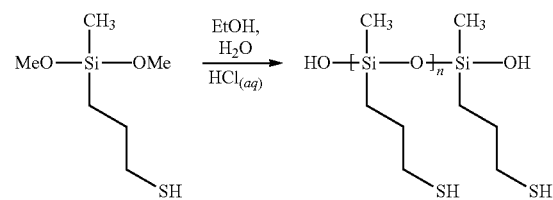

Synthesis of Poly(Mercaptopropylmethyl-Co-Acryloxypropylmethyl) Siloxane

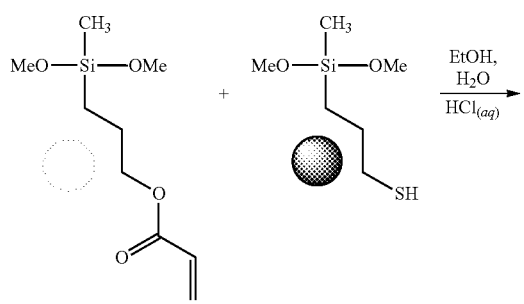

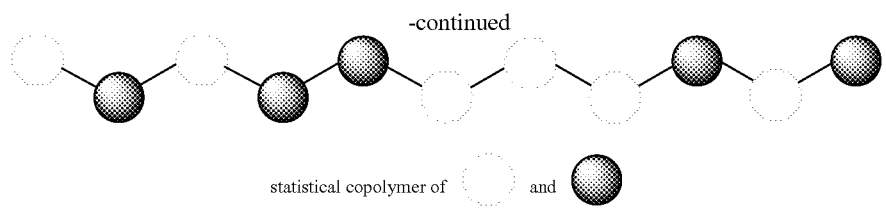

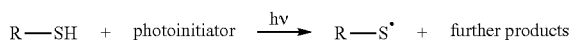

The molar mass distribution of the siloxanes was determined by means of gel permeation chromatography (universal calibration with polystyrene standard). The following results were obtained:

Poly(mercaptopropylmethyl) siloxane (3 hours of reaction time)
Molar mass: 200 g/mol-700 g/mol (2 to 5 units)
Poly(mercaptopropylmethyl) siloxane (9 hours of reaction time)
Molar mass: 200 g/mol-1400 g/mol (2 to 10 units)
Poly(mercaptopropylmethyl-co-acryloxypropylmethyl) siloxane (3 hours of reaction time)
Molar mass: 200 g/mol-1300 g/mol Preparation of the Latex Films and UV-Cross-Linking with Polymeric Siloxane Cross-Linking Agents The synthesized polymeric cross-linking agents are emulsified in different concentrations (1 to 4 phr) together with Lucirin TPO-L (1 phr) in deionized water containing Tween 20 (0.1 phr) and then added to the NR latex (40 drc). The latex mixture is doped with an antioxidant (0.5 phr Ionol LC) and stirred at room temperature for two hours. Then the films are prepared by means of the following coagulant dipping method:

washing of the ceramic formers and degreasing with acetone
preheating of the ceramic formers for at least 10 min in the drying oven at 120° C.
dipping of the former for 30 s in the coagulant bath at 70° C.
drying of the former for at least 1 min in the drying oven at 120° C.
dipping of the former in the NR latex mixture for 20 s
drying for 20 min in the drying oven at 120° C.
pulling off of the film The UV cross-linking of the NR latex films was carried out in the course of a UV exposure of the dried films (post-curing) with a UV source of Fusion UV Systems Inc. The UV exposure was carried out under air with a Ga-doped Hg source at a lamp power of 60% and a belt speed of 3.5 m/min. For three passes, the radiation dose corresponds to 15.6 J/cm².

It must be pointed out that the indicated parameters are to be understood not as limitative but merely as a way of showing how to manufacture the prophylactic article, for example, on the laboratory scale. In the large-scale industrial use, slightly different parameters may be necessary, but they can be found on the basis of a few experiments.

The following reaction mechanism constitutes the basis for the photochemical cross-linking with polymeric siloxane cross-linking agents.

(1) Initiation:

$$R\text{---}SH + \text{photoinitiator} \xrightarrow{h\nu} R\text{---}S^{\bullet} + \text{further products}$$

(2) Propagation:

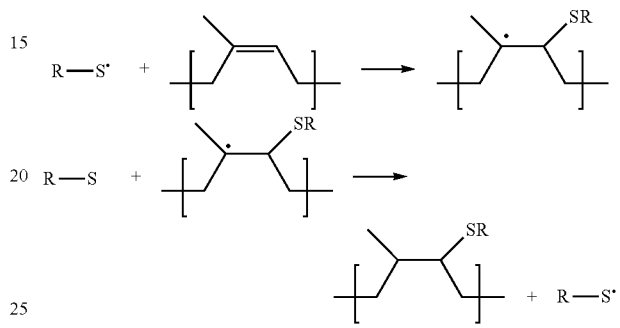

(3) Termination:

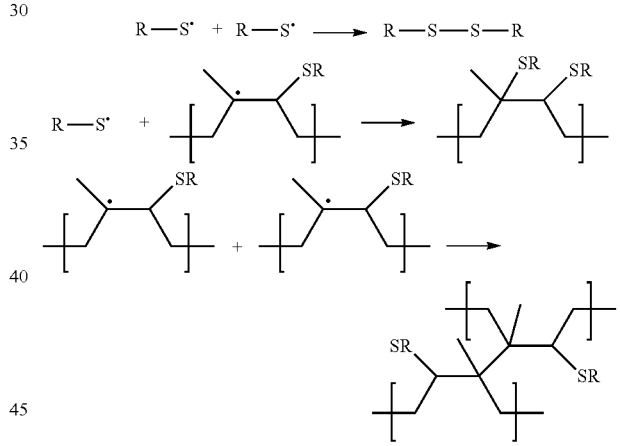

In general, the following parameters may be used for the UV cross-linking:

IR latices—Parameters for UV preliminary cross-linking in the falling film reactor: source power at 800 W-1000 W (800 W produces a mean radiation flux of ~500 mW/cm²), two exposure passes, conveyor speed (latex mixture) at 1.1 liters/min to 1.5 liters/min, solids content (latex) at 40% drc, photoinitiator concentration at 0.5 phr to 2 phr, thiol concentration at 0.5 phr to 2 phr.

NR latices—Parameters for UV preliminary cross-linking in the falling film reactor: source power at 2000 W-3500 W (3000 W produces a mean radiation flux of ~1690 mW/cm²), two exposure passes, conveyor speed (latex mixture) at 1.1 liters/min to 1.5 liters/min, solids content (latex) at 40% drc, photoinitiator concentration at 0.5 phr to 2 phr, thiol concentration at 1 phr to 5 phr.

General parameters for UV post-cross-linking: residual moisture content of the films preferably less than 20%. Post-dosing of 0.5 phr to 5 phr photoinitiator and 1 phr to 7.5 phr thiol, irradiation dose between 1 J/cm² and 25 J/cm² (240 nm-420 nm wavelength region).

The exposure is preferably carried out under air with a Ga-doped Hg source.

The structure of the polymeric cross-linking agent was determined by means of FT-IR spectroscopy and by means of thermogravimetric analysis (TGA). In the FT-IR spectra of the mercapto-functional siloxane homopolymers poly (mercaptopropyl) siloxane, poly(mercaptomethylpropyl) siloxane and poly(mercaptomethylmethyl) siloxane, a significant decrease of the Si—O—CH$_3$ band at approximately 2830 cm$^{-1}$ as well as the formation of OH groups (approximately 3370 cm$^{-1}$) can be observed, which can be attributed to a successful condensation reaction of the siloxane monomers (alkoxysilane monomers). Furthermore, the broadening of the Si—O band at approximately 1060 cm$^{-1}$ suggests the formation of a polymeric compound. The characteristic SH band (approximately 2558 cm$^{-1}$) is only weakly pronounced, since the infrared bands of thiol groups generally have a very low intensity. In the FT-IR spectrum of the copolymers poly(mercaptopropylmethyl-co-acryloxymethylpropyl) siloxane, the characteristic IR bands of the acrylate group (C=O bands at 1727 cm$^{-1}$ and C=C-bands at 1637 and 1622 mm$^{-1}$) are additionally detectable.

In the course of the TGA investigations, it was shown that the homopolymers and copolymers, depending on structure, are stable up to a temperature range of 240° C. to 270° C., and then exhibit a multi-stage decomposition.

In order to determine the reactivity of the polymeric cross-linking agents, a 2 wt % solution of polyisoprene standard in chloroform was prepared and doped with 1 phr Lucirin TPO-L and 5 phr of the corresponding thiol. The mixture was scraped onto CaF$_2$ plates, the solvent was evaporated and the thin layers were then exposed with a UV lamp (OmniCure Series 1000; high pressure lamp, full power: 100 W of EXPO). After different exposure times, IR spectra were recorded and the decrease of the normalized C=C band (835 cm$^{-1}$) over the exposure time was recorded. In comparison with the commercially available high-molecular thiol dipentaerythritol hexa(3-mercaptopropionate) (THIOCURE® Di-PETMP, Bruno Bock Thiochemicals), the siloxane polymers exhibit a substantially higher reactivity during the cross-linking. Whereas the relative decrease of the C=C bands amounts to approximately 5% after an exposure time of 150 s during use of THIOCURE® Di-PETMP, a decrease in the range of 12% can be achieved during use of poly(mercaptopropylmethyl) siloxane.

The reactivity of the polymeric cross-linker in the UV-initiated thiol-ene reaction was confirmed in further experiments. For this purpose, the cross-linking agents (1 phr) were mixed together with a photoinitiator (1 phr Lucirin TPO-L) in a polyisoprene standard solution (2 wt % in chloroform), and then thin films (40 µm) were scraped on, dried, exposed in structured manner and developed in chloroform. Similarly to the case of a negative resist, the exposed areas of the layer are cross-linked by the thiol-ene reaction and, during the subsequent development in chloroform, only the non-exposed areas are dissolved and removed. This experiment was carried out with a mask aligner at a very low exposure dose (~20 mW/cm², 80 s), in order to keep the influence of the direct C—C linking of the polymer chains by the photoinitiator radicals as slight as possible. The results show that a low concentration (1 phr) of the polymeric cross-linker is already sufficient to obtain a very high locally initiated cross-linking of the polyisoprene standard. The results therefore confirm the high reactivity and efficiency of the synthesized polymeric cross-linkers in the thiol-ene reaction.

On the basis of its chemical structure (high concentration of free Si—OH groups), poly(mercaptopropyl) siloxane can be cross-linked via a condensation reaction in the course of storage (even under inert atmosphere). The polymeric compound therefore possesses only a limited storage resistance (approximately 1 week). UV-cross-linked NR latex films (prior to aging and gamma sterilization) containing 1 and 2 phr cross-linking agent have a tear strength of 12 MPa-15 MPa.

In order to keep post-reactions (mainly cross-linking) as slight as possible during the storage of the polymeric cross-linking agents, disiloxane monomers were used in further synthesis batches. Due to the lower concentration of free Si—OH groups, the polymeric compound is characterized by a substantially greater storage resistance, and no change in the viscosity is observed even over a storage of 1 month (under inert atmosphere). The influence of different parameters (including reaction time, monomer content) during the synthesis on the corresponding mechanical strengths and aging resistances of NR latex films was further investigated.

In the first step, the synthesis of poly(mercaptopropylmethyl) siloxane at a constant monomer concentration in the reaction mixture (9% (w/v)) was stopped after different reaction times (3, 6 and 9 hours), the polymeric product was worked up and corresponding cross-linking experiments were carried out.

Figure 7:
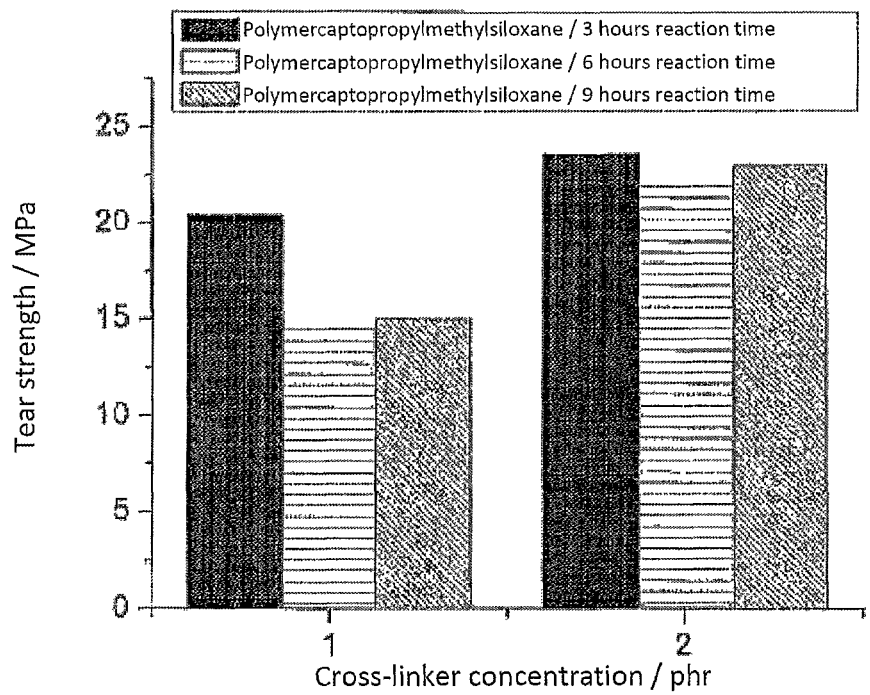
FIG. 7 shows the tear strengths of UV-cross-linked NR latex films (non-sterile/non-aged) at different poly(mercaptopropylmethyl) siloxane concentrations (synthesis time: 3, 6 and 9 h)
Figure 8:
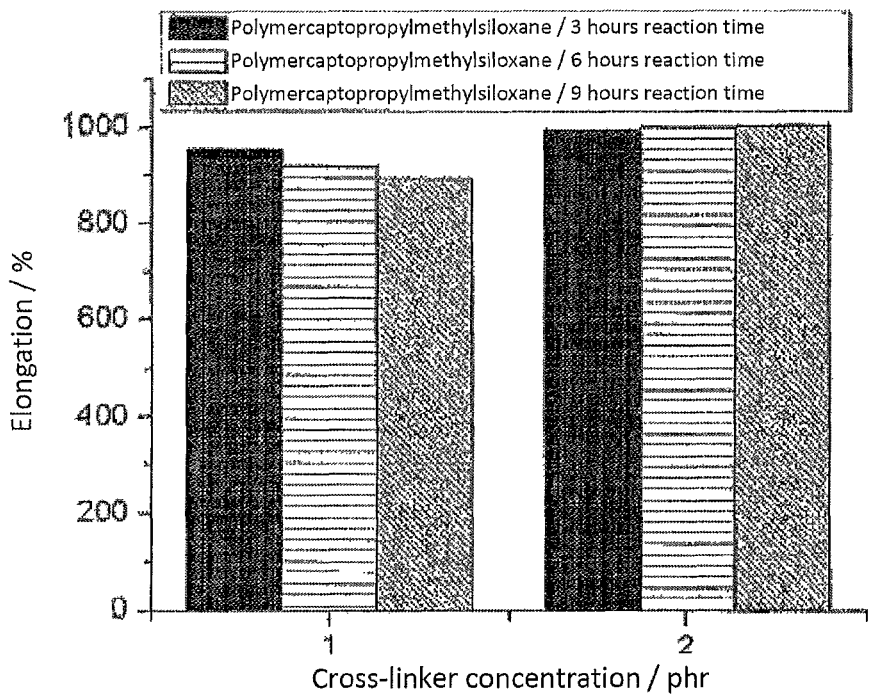
FIG. 8 shows the elongations at break of UV-cross-linked NR latex films (non-sterile/non-aged) at different poly(mercaptopropylmethyl) siloxane concentrations (synthesis time: 3, 6 and 9 h)
Figure 9:
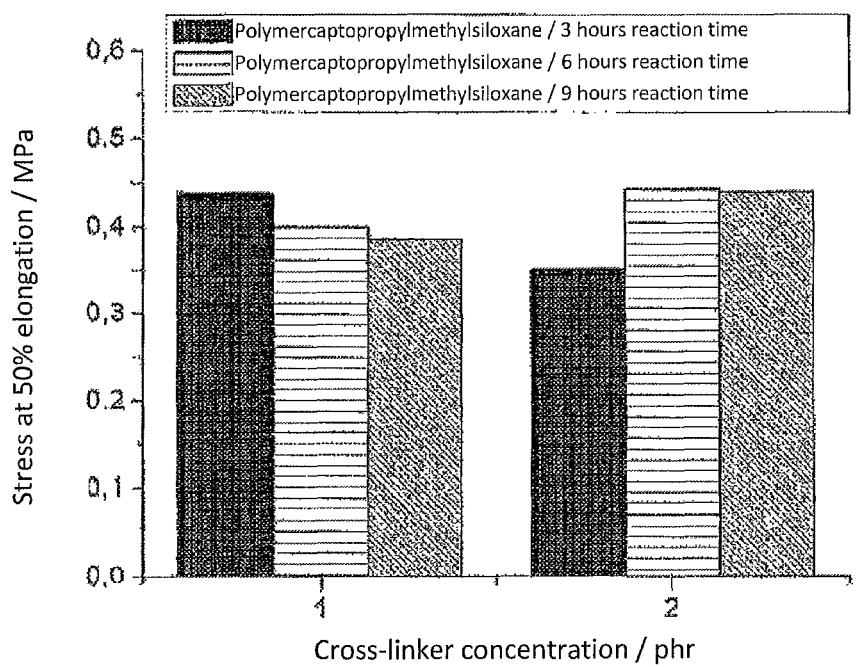
FIG. 9 shows the moduli (50% elongation) of UV-cross-linked NR latex films (non-sterile/non-aged) at different poly(mercaptopropylmethyl) siloxane concentrations (synthesis time: 3, 6 and 9 h)

At a cross-linking agent concentration of 1 phr, the polymer with the shorter reaction time (3 hours) exhibits the better mechanical strengths (20±2 MPa). At higher concentrations (2 phr) of the polymeric cross-linking agents, however, only a slight difference in the mechanical strengths can be observed, and the values lie in a range of 22 to 24 MPa. The results are plotted in FIGS. 7 to 9.

Figure 10:
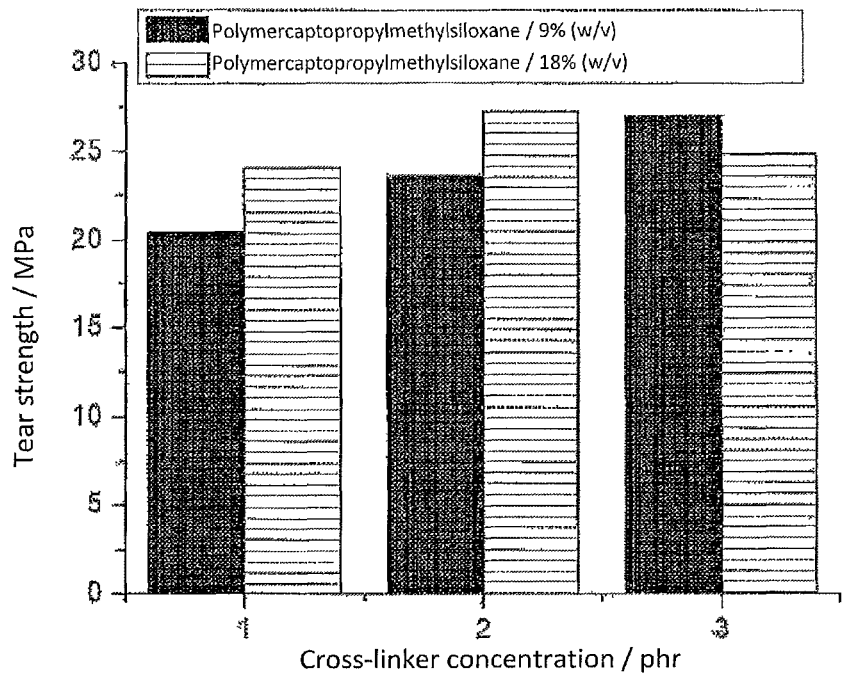
FIG. 10 shows the tear strengths of UV-cross-linked NR latex films (non-sterile/non-aged) at different poly(mercaptopropylmethyl) siloxane concentrations (monomer concentration: 9 and 18% (w/v))
Figure 11:
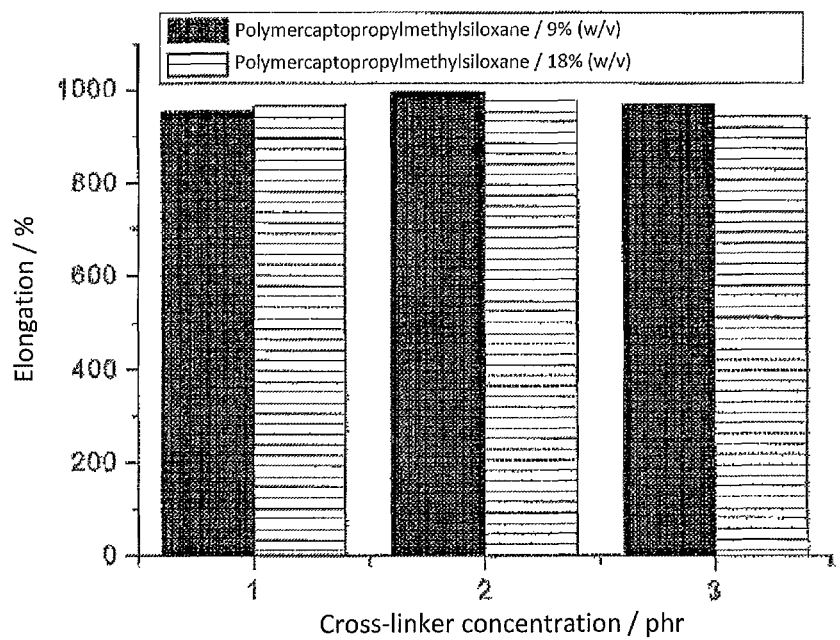
FIG. 11 shows the elongations at break of UV-cross-linked NR latex films (non-sterile/non-aged) at different poly(mercaptopropylmethyl) siloxane concentrations (monomer concentration: 9 and 18% (w/v))
Figure 12:
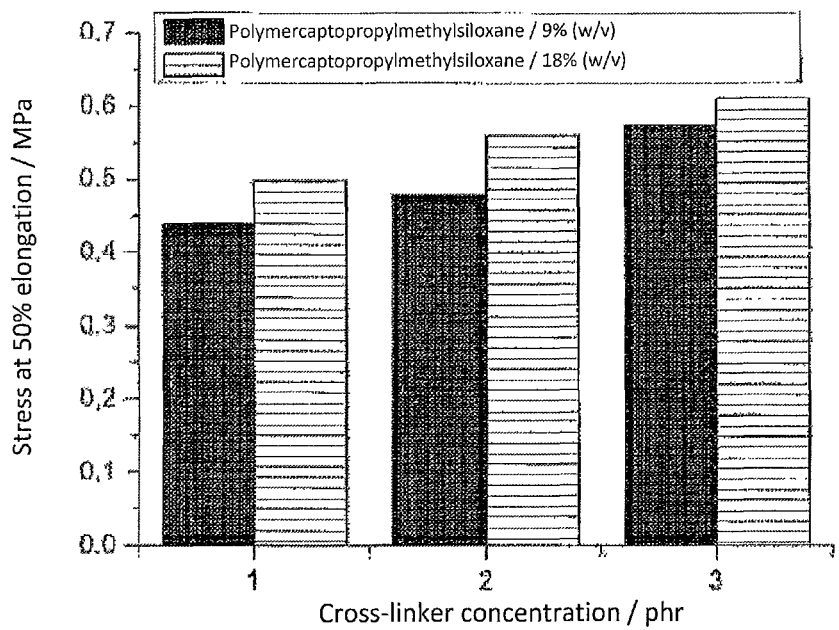
FIG. 12 shows the moduli (50% elongation) of UV-cross-linked NR latex films (non-sterile/non-aged) at different poly(mercaptopropylmethyl) siloxane concentrations (monomer concentration: 9 and 18% (w/v)).

In further-ranging studies, the monomer concentration during the synthesis was varied (9 and 18% (w/v)) at constant reaction time of 3 hours. Whereas, at lower monomer concentrations (9 (w/v)), an increase of the tear strength (from 20 to 26±2 MPa) can be observed with increasing cross-linker concentration in the latex mixture (from 1 to 3 phr), at a higher monomer concentration (18% (w/v)), an optimum (27±2 MPa) is achieved at 2 phr of the cross linker in the latex mixture. The results of this investigation are plotted in FIGS. 10 to 12.

In addition, NR latex films were prepared at higher concentrations of polymeric cross-linking agents and exposed to UV, and the influence of the cross-linking agent concentration on the mechanical properties was investigated. Poly(mercaptopropylmethyl) siloxane (monomer concentration: 18% (w/v); reaction time: 3 h) was selected as the polymeric cross-linking agent. The results permit the conclusion that a further increase of the cross-linking agent concentration from 3 phr to 4 phr does not lead to any significant improvement of the tear strengths. An increase of the stress value at 50% elongation can indeed be achieved, which suggests a higher-degree of cross-linking, but the tear strengths remain in the range of 25 MPa.

In a further step, a polymeric thiol cross-linking agent with shorter intermediate groups (between thiol group and polymeric main chain) was synthesized. Instead of the propyl group, a methyl group was selected. The monomer concentration during the synthesis was 9% (w/v) and the reaction time was three hours. This polymeric compound is also storage-stable, and no viscosity changes can be observed over a storage duration of one month.

With poly(mercaptomethylmethyl) siloxane as cross-linking agent, mechanical strengths that tend to be higher in comparison to poly(mercaptopropylmethyl) siloxane at the same cross-linking agent concentration (1 phr or 2 phr) can be achieved in the UV cross-linking of NR latex. For non-sterile and non-aged films, the tear strengths amount to approximately 23 MPa at a concentration of poly(mercaptopropylmethyl) siloxane of 1 phr and approximately 26 MPa at 2 phr. For non-sterile and non-aged films, the 50% moduli amount to approximately 0.45 MPa at a concentration of poly(mercaptopropylmethyl) siloxane of 1 phr and approximately 0.5 MPa at 2 phr.

Besides the mercapto-functional homopolymers, copolymers were also synthesized with acryloxypropylmethyl units and used as cross-linking agents in the UV cross-linking of NR latex. Due to the acrylate groups as a second monomer unit, on the one hand the formation of disulfides (as a side reaction of the thiol-ene reaction) should be suppressed and on the other hand a reactive group (acrylates) should be available for the binding of the polymeric cross-linking agent to the rubber chain. The concentration of both monomers during the synthesis was 9% (w/v) in total and the reaction time was three hours. This polymeric compound is also storage-stable, and no viscosity changes can be observed over a storage duration of one month. With the copolymer, significantly higher tear strengths (up to 30 MPa) can be achieved in comparison with the corresponding homopolymer (poly(mercaptopropylmethyl) siloxane) at the same cross-linking agent concentration in the latex mixture.

In further studies, the influence of the comonomer composition on the mechanical properties was investigated. For this purpose, the concentration of 3-acryloxypropylmethyl-siloxane was doubled from 8.4 to 16.8% (mol/total mol). The results of the tension test show that, with 2 phr P(MPMS-co-APMS), an increase of the acrylate units in the polymer chain is associated with a slight decrease of the mechanical properties by approximately 8%.

As reference, an acrylate homopolymer was also synthesized (analogously to the synthesis of the cross-linking agents indicated in the foregoing) and used as cross-linking agent. On the basis of the high reactivity of the acrylate groups, a photochemical cross-linking via direct C—C linking with the isoprene units is achieved. The successful structured exposure of polyisoprene films containing poly(acryloxypropylmethyl) siloxane as cross-linking agent can indeed suggest an adequately high reactivity in the UV cross-linking, but the mechanical properties of corresponding NR latex films (containing 1 phr and 2 phr cross-linking agent) are considerably lower (14 to 17 MPa) in comparison with the mercapto-functional homopolymers and copolymers. In addition, the films are characterized by an insufficient aging resistance (7 days of hot-air aging at 70° C.) (<3 MPa and strong yellowing).

In further experiments, the influence of the preliminary and post-cross-linking on the cross-linking of NR latex and IR latex with poly(mercaptomethylmethyl) siloxane as polymeric cross-linking agent was investigated.

Preliminary Cross-Linking:

The synthesized polymeric cross-linking agents (0.5 phr) were emulsified together with Lucirin TPO-L (0.5 phr) in deionized water containing Tween 20 (0.1 phr) and then added to the NR latex (40 drc) or to the IR latex (40 drc, Kraton). The latex mixture was stirred at room temperature for 2 hours. Then the respective latex mixture was cast into a Petri dish (approximately 1 mm layer thickness) and exposed with a UV source of Fusion UV Systems Inc. The NR latex mixtures were irradiated under air with a Ga-doped Hg source at a lamp power of 60% and a belt speed of 3.5 m/min in four passes (corresponds to a radiation dose of 20.8 J/cm$^2$). The IR latex mixtures were irradiated under air with a Ga-doped Hg source at a lamp power of 60% and a belt speed of 3.5 m/min in two passes (corresponds to a radiation dose of 10.4 J/cm$^2$).

During the preparation of preliminarily cross-linked films (without subsequent post-cross-linking), the latex mixture was doped with the antioxidant (0.5 phr Ionol LC) after the preliminary cross-linking and stirred at room temperature for 2 hours. Then the dipping of the latex films was carried out by means of the coagulant dipping method. In the process, the following working steps are performed:
  washing of the ceramic formers and degreasing with acetone
  preheating of the ceramic formers for at least 10 minutes in the drying oven at 120° C.
  dipping of the former for 30 seconds in the coagulant bath at 70° C.
  drying of the former for at least 1 minute in the drying oven at 120° C.
  dipping of the former in the NR latex mixture for 20 seconds
  drying for 20 minutes in the drying oven at 120° C.
  pulling off Post-Cross-Linking:

Optionally, a post-cross-linking was also performed. In this case, the respective latex mixtures (preliminarily cross-linked or not preliminarily cross-linked) were doped with an emulsion consisting of the synthesized polymeric cross-linking agents (2 phr), Lucirin TPO-L (1 phr), deionized water (2 phr) and Tween 20 (0.1 phr). Then the latex mixture was doped with an antioxidant (0.5 phr Ionol LC) and stirred at room temperature for 2 hours.

Corresponding films were prepared by means of the coagulant dipping method and the post-cross-linking was carried out in the course of a UV exposure of the dried films (post-curing) with a UV source of Fusion UV Systems Inc. Both NR latex films and IR latex films were irradiated under air with a Ga-doped Hg source at a lamp power of 60% and a belt speed of 3.5 m/min in three passes (corresponds to a radiation dose of 15.6 J/cm$^2$).

During the photochemical cross-linking of the NR latex, it was found that the highest mechanical strengths can be achieved by a post-cross-linking. The tear strength of the NR latex films (non-sterile, non-aged) was approximately 22.5 MPa for the preliminarily cross-linked sample, approximately 18 MPa for the preliminarily and post-cross-linked sample and approximately 25 MPa for the exclusively post-cross-linked sample. This result is surprising, inasmuch as the preliminarily and post-cross-linked sample exhibited the lowest tear strength.

A comparable trend is also observed during the UV preliminary cross-linking of IR latex. In this case, the tear strength of preliminarily cross-linked IR latex films lies in the range of 3.5 MPa. In contrast to NR latex films, however, a distinct increase of the tear strengths to 16 MPa is possible by a combined preliminary and post-cross-linking.

For further evaluation of the polymeric cross-linking agents, further mercapto polymers were synthesized. For this purpose, the preparation of poly(mercaptomethylm-ethyl) siloxane and poly(mercaptopropylmethyl-co-acryloxypropylmethyl) siloxane in the presence of 2 phr or 3 phr methoxytrimethylsilane as terminating agent was carried out for a controlled polymerization (preparation of polymers with lower polydispersity index). The synthesis was carried out analogously to the synthesis described in the foregoing, wherein 2 phr or 3 phr methoxytrimethylsilane (Sigma-Aldrich) was additionally added to the reaction mixture.

The tear strengths of the UV post-cross-linked NR latex films (non-sterile, non-aged) lie consistently between 25 MPa and 27 MPa.

For determination of the extractable cross-linking agent concentration, post-cross-linked NR latex films were extracted in the course of a Soxhlet extraction (10 hours/toluene). The solvent was drawn off by means of rotary evaporation and the extract was dried to constant weight in the vacuum drying oven at 35° C. and 100 mbar.

By means of C/H/N/S, the extractable S compounds (thiols and proteins of the NR latex) were determined in a triplicate determination.

The results of the elemental analysis reveal a significantly lower extractability (75%) of the cross-linking agent in comparison with lower-molecular thiols (such as, for example, trimethylolpropane trimercaptopropionate, TMPMP).

TABLE 3

S concentration in the extract of UV post-cross-linked NR latex films

| Sample | Photoinitiator | Thiol | Extractable S content/mg S/g latex |
|---|---|---|---|
| Reference | Lucirin TPO-L (1 phr) | TMPMP (2 phr) | 2.074 |
| Homopolymer | Lucirin TPO-L (1 phr) | Poly(mercapto-propylmethylmethyl) siloxane (2 phr) | 0.534 |
| Copolymer | Lucirin TPO-L (1 phr) | Poly(mercapto-propylmethyl-co-acryloxypropylmethyl) siloxane (2 phr) | 0.522 |

In the following exemplary embodiments, it is to be shown that the thermal cross-linking of XNBR latex films is possible not only with polar, water-soluble epoxy cross-linking agents but also with non-polar epoxy derivatives.

Example A—Cross-Linking with Bisphenol A Diglycidyl Ether 3 phr bisphenol A diglycidyl ether (Huntsman) is emulsified in 6 phr deionized water containing 0.3 phr Tween 20. Then the emulsion is added to the latex mixture (pH=10.2; ~25 drc) and the latex mixture is stirred at room temperature for 60 minutes. The films are prepared analogously to the described procedure and the thermal cross-linking takes place in the course of the drying of the films in the circulating-air oven.

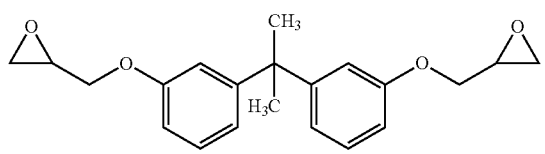 [SMILES: CC(C)(c1cccc(OCC2CO2)c1)c1cccc(OCC2CO2)c1]

Bisphenol A diglycidyl Ether

Example B—Cross-Linking with a Hydrogenated Bisphenol A Diglycidyl Ether

The preparation takes place analogously to Example A—except, instead of the bisphenol A diglycidyl ether, 3 phr and 5 phr respectively of a hydrogenated bisphenol A diglycidyl ether (EPALLOY®5000 and EPALLOY®5001 respectively of CVC Thermoset Specialities) is used.

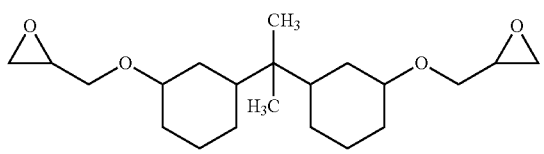 [SMILES: CC(C)(C1CCCC(OCC2CO2)C1)C1CCCC(OCC2CO2)C1]

Hydrogenated Bisphenol A Diglycidyl Ether

Example C—Cross-Linking with a Hexahydrophthalic Acid Diglycidyl Ether

The preparation takes place analogously to Example A—except, instead of the bisphenol A diglycidyl ether, a hexahydrophthalic acid diglycidyl ether (3 phr and 5 phr EPALLOY®5200 of CVC Thermoset Specialities) is used.

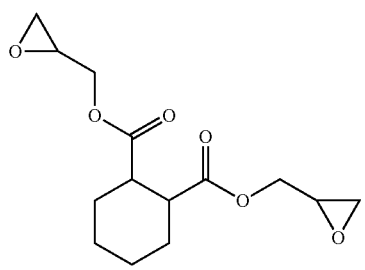 [SMILES: O=C(OCC1CO1)C1CCCCC1C(=O)OCC1CO1]

Hexahydrophthalic Acid Diglycidyl Ether

Example D—Cross-Linking with a 1,4-Cyclohexanedimethanol Diglycidyl Ether

The preparation takes place analogously to Example A—except, instead of the bisphenol A diglycidyl ether, a 1,4-cyclohexanedimethanol diglycidyl ether (3 phr and 5 phr ERISYS™ GE 22 of CVC Thermoset Specialities) is used.

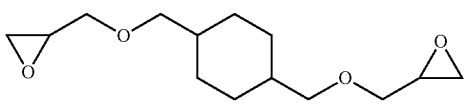 [SMILES: C1CC(COCC2CO2)CCC1COCC1CO1]

1,4-Cyclohexanedimethanol Diglycidyl Ether

The measured mechanical properties of the XNBR latices cross-linked according to Examples A-D are summarized in Table 4.

TABLE 4

Mechanical properties of thermally cross-linked XNBR latex films during use of different epoxides

| Epoxy cross-linker | Concentration of cross-linker [phr] | Tear strength [MPa] | Stress [%] | Stress at 50% elongation [MPa] |
|---|---|---|---|---|
| Bisphenol A diglycidyl ether | 3 | 42.2 | 700 | 1.58 |

TABLE 4-continued

Mechanical properties of thermally cross-linked XNBR latex films during use of different epoxies

| Epoxy cross-linker | Concentration of cross-linker [phr] | Tear strength [MPa] | Stress [%] | Stress at 50% elongation [MPa] |
|---|---|---|---|---|
| EPALLOY ® 5000 | 3 | 39.3 | 700 | 1.53 |
| EPALLOY ® 5000 | 5 | 39.9 | 670 | 1.53 |
| EPALLOY ® 5001 | 3 | 36.9 | 680 | 1.62 |
| EPALLOY ® 5001 | 5 | 38.4 | 670 | 1.59 |
| EPALLOY ® 5200 | 3 | 36.8 | 690 | 1.59 |
| EPALLOY ® 5200 | 5 | 38.4 | 690 | 1.46 |
| ERISYS ™ GE22 | 3 | 34.0 | 680 | 1.60 |
| ERISYS ™ GE22 | 5 | 34.9 | 670 | 1.48 |

The exemplary embodiments describe possible embodiment variants of the method; diverse combinations of the individual embodiment variants with one another are also possible.

The invention claimed is:

1. A method for the manufacture of a prophylactic article from a (carboxylated) diene rubber, according to which at least one layer of a (carboxylated) diene latex is applied on a former and the (carboxylated) diene latex is cross-linked exclusively with a monomeric or polymeric cross-linking agent comprising an organic monomer or polymer having a molar mass between 170 g/mol and 4000 g/mol,
wherein the monomeric or polymeric cross-linking agent is added to the (carboxylated) diene latex and dissolved therein or emulsified or dispersed therein,
wherein:
(a) the monomeric or polymeric cross-linking agent is selected from a group consisting of multifunctional epoxies, multifunctional silanes, multifunctional siloxanes, multifunctional polymer thiols, as well as mixtures thereof; and
(b) the monomeric or polymeric cross-linking agent is a polymeric cross-linking agent comprising a mercapto-functional siloxane polymer.

2. The method according to claim 1, wherein the cross-linking of the (carboxylated) diene latex molecules is achieved thermally and/or photochemically by means of ultraviolet radiation.

3. The method according to claim 1, wherein the pH of the (carboxylated) diene latex is adjusted to a value of greater than/equal to 9.

4. The method according to claim 1, wherein the mercapto-functional siloxane polymer is added as emulsion to the (carboxylated) diene latex.

5. The method according to claim 1, wherein a mercapto-functional siloxane homopolymer or a copolymer of the mercapto-functional siloxane homopolymer with an acrylic siloxane is used as the mercapto-functional siloxane polymer.

6. The method according to claim 5, wherein a mercapto-functional siloxane homopolymer with the structural formula

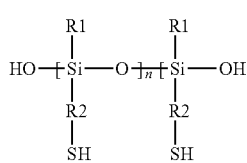

is used, wherein R1 stands for a first unit selected from a first group consisting of —CH₃, —OH, —C₂H₅, —C₃H₇, aromatic groups, R2 for a second unit selected from a second group consisting of —CH₂, C₂H₄, C₃H₆; —(CH₂)₁₁—, aromatic groups, and —CH₂-aromatic groups.

7. The method according to claim 5, wherein a mercapto-functional siloxane copolymer with the structural formula

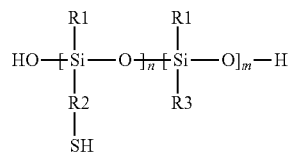

is used, wherein R1 stands for a first unit selected from a first group consisting of —CH₃, —OH, —C₂H₅, —C₃H₇, aromatic groups, R2 for a second unit selected from a second group consisting of —CH₂, C₂H₄, C₃H₆; —(CH₂)₁₁—, aromatic groups, —CH₂-aromatic groups, and R3 for a third unit, selected from a third group consisting of alkyl groups, —CH₂— aromatic, aromatic groups, alkene groups, methacryloxypropyl-, acryloxypropyl-, and epoxy groups.

8. The method according to claim 1, wherein a silane with the structural formula

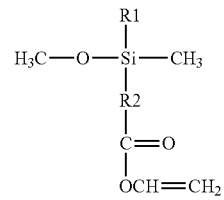

is used as the cross-linking agent, wherein R1 stands for a first unit selected from a first group consisting of —OH, —CH₃, —C₂H₅, —C₃H₇, aromatic groups, R2 for a second unit selected from a second group consisting of —CH₂, C₂H₄, C₃H₆, and aromatic groups.

9. The method according to claim 5, wherein the mercapto-functional siloxane homopolymer is selected from a group consisting of poly(mercaptopropyl) siloxane, poly(mercaptomethylpropyl)siloxane, poly(mercaptomethylmethyl) siloxane, poly(mercaptoethylmethyl) siloxane, poly(mercaptomethylethyl) siloxane, poly(mercaptopropylmethyl) siloxane, poly(mercaptomethylbenzyl) siloxane, poly(mercaptopropylbenzyl) siloxane, poly(mercaptoethylbenzyl) siloxane and/or wherein the copolymer of the mercapto-functional siloxane homopolymer with an acrylic siloxane is selected from a group consisting of poly(mercaptopropylmethyl-co-acryloxypropylmethyl) siloxane, poly(mercaptomethylmethyl-co-acryloxymethylpropyl) siloxane, poly(mercaptomethylmethyl-co-acryloxypropylmethyl) siloxane, poly(mercaptomethylmethyl-co-acryloxypropylethyl) siloxane, poly(mercaptomethylmethyl-co-acryloxyethylpropyl) siloxane, poly(mercaptomethylmethyl-co-acryloxymethylmethyl) siloxane, poly(mercaptomethylmethyl-co-acryloxypropyl) siloxane, poly(mercaptomethylmethyl-co-acryloxyethyl) siloxane, poly(mercaptomethylmethyl-co-acryloxymethyl) siloxane, and poly(mercaptopropylmethyl-co-acryloxymethylpropyl) siloxane.

10. The method according to claim 5, wherein the proportion of mercapto-functional siloxane polymer in the copolymer of the mercapto-functional siloxane polymer with an acrylic siloxane is at least 20 wt %.

11. The method according to claim 1, wherein the cross-linking agent is added to the (carboxylated) diene latex in a proportion of 1 phr to 10 phr relative to the total composition of the (carboxylated) diene latex.

12. The method according to claim 1, wherein the prophylactic article is a glove.

13. A prophylactic article comprising a layer of a (carboxylated) diene elastomer, wherein the (carboxylated) diene elastomer molecular chains of the (carboxylated) diene elastomer are cross-linked covalently via at least one polymer, wherein the at least one polymer is a mercapto-functional siloxane polymer.

14. The prophylactic article according to claim 13, wherein the prophylactic article is a glove.

* * * * *